US008263091B2

(12) United States Patent
Klinman et al.

(10) Patent No.: US 8,263,091 B2
(45) Date of Patent: Sep. 11, 2012

(54) METHOD OF TREATING AND PREVENTING INFECTIONS IN IMMUNOCOMPROMISED SUBJECTS WITH IMMUNOSTIMULATORY CPG OLIGONUCLEOTIDES

(75) Inventors: Dennis M. Klinman, Potomac, MD (US); Daniela Verthelyi, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1663 days.

(21) Appl. No.: 10/666,022

(22) Filed: Sep. 17, 2003

(65) Prior Publication Data

US 2004/0105872 A1 Jun. 3, 2004

Related U.S. Application Data

(60) Provisional application No. 60/411,944, filed on Sep. 18, 2002.

(51) Int. Cl.
*A61K 31/70* (2006.01)
(52) U.S. Cl. ............... 424/278.1; 424/184.1; 424/190.1; 536/23.1; 536/25.6
(58) Field of Classification Search ................... None
See application file for complete search history.

(56) References Cited

U.S. PATENT DOCUMENTS

| | | |
|---|---|---|
| 2,215,233 A | 9/1940 | Ruskin |
| 3,906,092 A | 9/1975 | Hilleman et al. |
| 3,911,117 A | 10/1975 | Ender |
| 3,914,450 A | 10/1975 | Robbins et al. |
| 4,469,863 A | 9/1984 | Ts'o |
| 4,544,559 A | 10/1985 | Gil et al. |
| 4,741,914 A | 5/1988 | Kimizuka et al. |
| 4,758,553 A | 7/1988 | Ogoshi |
| 4,806,376 A | 2/1989 | Saeki et al. |
| 4,956,296 A | 9/1990 | Fahnestock |
| 4,963,387 A | 10/1990 | Nakagawa et al. |
| 4,994,442 A | 2/1991 | Gil et al. |
| 5,023,243 A | 6/1991 | Tullis |
| 5,066,500 A | 11/1991 | Gil et al. |
| 5,175,267 A * | 12/1992 | Chu ............................ 536/26.3 |
| 5,231,085 A | 7/1993 | Alexander et al. |
| 5,234,811 A | 8/1993 | Beutler et al. |
| 5,248,670 A | 9/1993 | Draper et al. |
| 5,268,365 A | 12/1993 | Rudolph et al. |
| 5,288,509 A | 2/1994 | Potman et al. |
| 5,488,039 A | 1/1996 | Masor et al. |
| 5,492,899 A | 2/1996 | Masor et al. |
| 5,585,479 A | 12/1996 | Hoke et al. |
| 5,591,721 A | 1/1997 | Agrawal et al. |
| 5,602,109 A | 2/1997 | Masor et al. |
| 5,612,060 A | 3/1997 | Alexander |
| 5,614,191 A | 3/1997 | Puri et al. |
| 5,650,156 A | 7/1997 | Grinstaff et al. |
| 5,663,153 A | 9/1997 | Hutcherson et al. |
| 5,679,397 A | 10/1997 | Kuroda et al. |
| 5,684,147 A | 11/1997 | Agrawal et al. |
| 5,700,590 A | 12/1997 | Masor et al. |
| 5,712,256 A | 1/1998 | Kulkarni et al. |
| 5,723,335 A | 3/1998 | Hutcherson et al. |
| 5,786,189 A | 7/1998 | Loct et al. |
| 5,804,566 A | 9/1998 | Carson et al. |
| 5,840,705 A | 11/1998 | Tsukada |
| 5,849,719 A | 12/1998 | Carson et al. |
| 5,895,652 A | 4/1999 | Giampapa |
| 5,919,456 A | 7/1999 | Puri et al. |
| 5,922,766 A | 7/1999 | Acosta et al. |
| 5,976,580 A | 11/1999 | Ivey et al. |
| 5,980,958 A | 11/1999 | Naylor et al. |
| 5,994,126 A | 11/1999 | Steinman et al. |
| 6,022,853 A | 2/2000 | Kuberasampath et al. |
| 6,194,388 B1 | 2/2001 | Krieg |
| 6,207,646 B1 | 3/2001 | Krieg |
| 6,214,806 B1 | 4/2001 | Krieg |
| 6,218,371 B1 | 4/2001 | Krieg |
| 6,239,116 B1 | 5/2001 | Krieg |
| 6,326,007 B1 * | 12/2001 | Yilma et al. ............... 424/207.1 |
| 6,339,068 B1 | 1/2002 | Krieg |
| 6,406,705 B1 | 6/2002 | Davis |
| 6,423,539 B2 | 7/2002 | Fong et al. |
| 6,428,788 B1 | 8/2002 | Debinski et al. |
| 6,429,199 B1 | 8/2002 | Krieg |
| 6,498,148 B1 | 12/2002 | Raz |
| 6,514,948 B1 | 2/2003 | Raz et al. |
| 6,534,062 B2 | 3/2003 | Raz et al. |
| 6,552,006 B2 * | 4/2003 | Raz et al. .................... 514/44 R |

(Continued)

FOREIGN PATENT DOCUMENTS

EP 0 286 224 10/1988

(Continued)

OTHER PUBLICATIONS

Fraternale et al. (2000) JAIDS. 23: 209-220.*
Horner et al. (2001) Journal of Immunology. 167: 1584-1591.*
Calarota et al (1999) Journal of Immunology. 162: 2330-2338.*
Walker et al (1999) PNAS. 96: 6970-6975.*
Klinman (2004) Nature Reviews. 4: 1-10.*
Krieg et al (1998) Journal of Immunology. 161: 2428-2434.*
Lu et al. SIV DNA vaccine trial in macaques: post-challenge necropsy in vaccine and control groups. Vaccine. Jun. 1997;15(8):920-3.*
Cho et al. Immunostimulatory DNA-based vaccines induce cytotoxic lymphocyte activity by a T-helper cell-independent mechanism. Nat Biotechnol. May 2000;18(5):509-14.*

(Continued)

*Primary Examiner* — Zachariah Lucas
*Assistant Examiner* — Michelle S Horning
(74) *Attorney, Agent, or Firm* — Klarquist Sparkman, LLP

(57) ABSTRACT

A method is disclosed herein for increasing an immune response to an opportunistic infection in an immunocompromised subject. In one embodiment, the subject is infected with a lentivirus. The method includes increasing an immune response to a pathogen using D oligodeoxynucleotides including a CpG motif.

12 Claims, 9 Drawing Sheets

U.S. PATENT DOCUMENTS

| | | | |
|---|---|---|---|
| 6,562,798 B1 | 5/2003 | Schwartz | |
| 6,589,940 B1 | 7/2003 | Raz et al. | |
| 6,610,661 B1 | 8/2003 | Carson et al. | |
| 6,613,751 B2 | 9/2003 | Raz et al. | |
| 6,653,292 B1 | 11/2003 | Krieg et al. | |
| 6,977,245 B2* | 12/2005 | Klinman et al. | 514/44 R |
| 2001/0034330 A1 | 10/2001 | Kensil | |
| 2001/0036462 A1 | 11/2001 | Fong et al. | |
| 2001/0044416 A1 | 11/2001 | McCluskie et al. | |
| 2001/0046967 A1 | 11/2001 | Van Nest | |
| 2002/0006403 A1 | 1/2002 | Yu et al. | |
| 2002/0028784 A1 | 3/2002 | Van Nest | |
| 2002/0042383 A1 | 4/2002 | Yew et al. | |
| 2002/0042387 A1 | 4/2002 | Raz et al. | |
| 2002/0055477 A1 | 5/2002 | Van Nest et al. | |
| 2002/0064515 A1 | 5/2002 | Krieg et al. | |
| 2002/0065236 A1 | 5/2002 | Yew et al. | |
| 2002/0086295 A1 | 7/2002 | Raz et al. | |
| 2002/0086839 A1 | 7/2002 | Raz et al. | |
| 2002/0090724 A1 | 7/2002 | Taylor et al. | |
| 2002/0091095 A1 | 7/2002 | Phillips et al. | |
| 2002/0091097 A1 | 7/2002 | Bratzler et al. | |
| 2002/0098199 A1 | 7/2002 | Van Nest et al. | |
| 2002/0098205 A1 | 7/2002 | Choi et al. | |
| 2002/0098980 A1 | 7/2002 | Choi et al. | |
| 2002/0107212 A1 | 8/2002 | Van Nest et al. | |
| 2002/0110569 A1 | 8/2002 | Granoff et al. | |
| 2002/0111323 A1 | 8/2002 | Martin et al. | |
| 2002/0136776 A1 | 9/2002 | Fang et al. | |
| 2002/0137714 A1 | 9/2002 | Kandimalla et al. | |
| 2002/0142974 A1 | 10/2002 | Kohn et al. | |
| 2002/0142977 A1 | 10/2002 | Raz et al. | |
| 2002/0142978 A1 | 10/2002 | Raz et al. | |
| 2002/0156033 A1 | 10/2002 | Bratzler et al. | |
| 2002/0164341 A1 | 11/2002 | Davis et al. | |
| 2002/0165178 A1 | 11/2002 | Schetter et al. | |
| 2002/0183272 A1 | 12/2002 | Johnston et al. | |
| 2002/0197269 A1 | 12/2002 | Lingnau et al. | |
| 2002/0198165 A1 | 12/2002 | Bratzler et al. | |
| 2003/0003579 A1 | 1/2003 | Kadowaki et al. | |
| 2003/0022849 A1 | 1/2003 | Chang | |
| 2003/0022852 A1 | 1/2003 | Van Nest et al. | |
| 2003/0026782 A1 | 2/2003 | Krieg | |
| 2003/0026801 A1 | 2/2003 | Weiner et al. | |
| 2003/0049266 A1 | 3/2003 | Fearon et al. | |
| 2003/0050261 A1 | 3/2003 | Krieg et al. | |
| 2003/0050263 A1 | 3/2003 | Krieg et al. | |
| 2003/0050268 A1 | 3/2003 | Krieg et al. | |
| 2003/0052839 A1 | 3/2003 | Binley et al. | |
| 2003/0055014 A1 | 3/2003 | Bratzler | |
| 2003/0059773 A1 | 3/2003 | Van Nest et al. | |
| 2003/0060440 A1 | 3/2003 | Klinman et al. | |
| 2003/0064064 A1 | 4/2003 | Dina | |
| 2003/0072762 A1 | 4/2003 | Van de Winkel et al. | |
| 2003/0073142 A1 | 4/2003 | Chen et al. | |
| 2003/0078223 A1 | 4/2003 | Raz et al. | |
| 2003/0091599 A1 | 5/2003 | Davis et al. | |
| 2003/0092663 A1 | 5/2003 | Raz | |
| 2003/0096417 A1 | 5/2003 | Fischer | |
| 2003/0100527 A1 | 5/2003 | Krieg et al. | |
| 2003/0104044 A1 | 6/2003 | Semple et al. | |
| 2003/0104523 A1 | 6/2003 | Lipford et al. | |
| 2003/0109469 A1 | 6/2003 | Carson et al. | |
| 2003/0119773 A1 | 6/2003 | Raz et al. | |
| 2003/0119774 A1 | 6/2003 | Foldvari et al. | |
| 2003/0119776 A1 | 6/2003 | Phillips et al. | |
| 2003/0125284 A1 | 7/2003 | Raz et al. | |
| 2003/0129251 A1 | 7/2003 | Van Nest et al. | |
| 2003/0130217 A1 | 7/2003 | Raz et al. | |
| 2003/0133988 A1 | 7/2003 | Fearon et al. | |
| 2003/0135875 A1 | 7/2003 | Ehrhardt et al. | |
| 2003/0138413 A1 | 7/2003 | Vicari et al. | |
| 2003/0138453 A1 | 7/2003 | O'Hagan et al. | |
| 2003/0139364 A1 | 7/2003 | Krieg et al. | |
| 2003/0143213 A1 | 7/2003 | Raz et al. | |
| 2003/0143743 A1 | 7/2003 | Schuler et al. | |
| 2003/0144229 A1 | 7/2003 | Klinman et al. | |
| 2003/0147870 A1 | 8/2003 | Raz et al. | |
| 2003/0148316 A1 | 8/2003 | Lipford et al. | |
| 2003/0148976 A1 | 8/2003 | Krieg et al. | |
| 2003/0148983 A1 | 8/2003 | Fontoura et al. | |
| 2003/0157717 A1 | 8/2003 | Draghia-Akli | |
| 2003/0158136 A1 | 8/2003 | Rice et al. | |
| 2003/0165478 A1 | 9/2003 | Sokoll | |
| 2003/0166001 A1 | 9/2003 | Lipford | |
| 2003/0170273 A1 | 9/2003 | O'Hagan et al. | |
| 2003/0171321 A1 | 9/2003 | Schmidt et al. | |
| 2003/0175731 A1 | 9/2003 | Fearon et al. | |
| 2003/0176373 A1 | 9/2003 | Raz et al. | |
| 2003/0176389 A1 | 9/2003 | Raz et al. | |
| 2003/0180320 A1 | 9/2003 | Darji et al. | |
| 2003/0181406 A1 | 9/2003 | Schetter et al. | |
| 2003/0185848 A1 | 10/2003 | Johnston et al. | |
| 2003/0185900 A1 | 10/2003 | Choi et al. | |
| 2003/0186921 A1 | 10/2003 | Carson et al. | |
| 2003/0191079 A1 | 10/2003 | Krieg et al. | |
| 2003/0199466 A1 | 10/2003 | Fearon et al. | |
| 2003/0203861 A1 | 10/2003 | Carson et al. | |
| 2003/0206967 A1 | 11/2003 | Choi et al. | |
| 2003/0207287 A1 | 11/2003 | Short | |
| 2003/0212026 A1 | 11/2003 | Krieg et al. | |
| 2003/0212028 A1 | 11/2003 | Raz et al. | |
| 2003/0216340 A1 | 11/2003 | Van Nest et al. | |
| 2003/0219752 A1 | 11/2003 | Short | |
| 2003/0220277 A1 | 11/2003 | Yew et al. | |
| 2003/0224010 A1 | 12/2003 | Davis et al. | |
| 2003/0225016 A1 | 12/2003 | Fearon et al. | |
| 2003/0232780 A1 | 12/2003 | Carson et al. | |
| 2004/0005588 A1 | 1/2004 | Cohen et al. | |
| 2004/0006010 A1 | 1/2004 | Carson et al. | |
| 2004/0006032 A1 | 1/2004 | Lopez | |
| 2004/0006034 A1 | 1/2004 | Raz et al. | |
| 2004/0009897 A1 | 1/2004 | Sokoll | |
| 2004/0009942 A1 | 1/2004 | Van Nest | |
| 2004/0009949 A1 | 1/2004 | Krieg | |
| 2004/0013686 A1 | 1/2004 | Granoff et al. | |
| 2004/0013688 A1 | 1/2004 | Wise et al. | |
| 2004/0028693 A1 | 2/2004 | Wu et al. | |
| 2004/0052763 A1* | 3/2004 | Mond et al. | 424/93.2 |
| 2006/0189550 A1* | 8/2006 | Jiang et al. | 514/26 |

FOREIGN PATENT DOCUMENTS

| | | |
|---|---|---|
| EP | 0 302 758 | 11/1989 |
| EP | 0 468 520 A2 | 1/1991 |
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 91/12811 | 9/1991 |
| WO | WO 92/03456 | 4/1992 |
| WO | WO 92/18522 | 10/1992 |
| WO | WO 92/21353 | 12/1992 |
| WO | WO 93/17115 | 9/1993 |
| WO | WO 94/19945 | 9/1994 |
| WO | WO 95/05853 | 3/1995 |
| WO | WO 95/18231 | 7/1995 |
| WO | WO 95/26204 | 10/1995 |
| WO | WO 96/02555 | 2/1996 |
| WO | WO 96/24380 | 2/1996 |
| WO | WO 96/35782 | 11/1996 |
| WO | WO 97/28259 | 1/1997 |
| WO | WO 98/29430 | 12/1997 |
| WO | WO 98/11211 | 3/1998 |
| WO | WO 98/14210 | 4/1998 |
| WO | WO 98/16247 | 4/1998 |
| WO | WO 98/18810 | 5/1998 |
| WO | WO 98/32462 | 7/1998 |
| WO | WO 98/37919 | 9/1998 |
| WO | WO 98/40100 | 9/1998 |
| WO | WO 98/49288 | 11/1998 |
| WO | WO 98/49348 | 11/1998 |
| WO | WO 98/52581 | 11/1998 |
| WO | WO 98/55495 | 12/1998 |
| WO | WO 99/11275 | 3/1999 |
| WO | WO 99/37151 | 7/1999 |
| WO | WO 99/51259 | 10/1999 |
| WO | WO 99/56755 | 11/1999 |

| WO | WO 99/58118 | 11/1999 |
| WO | WO 99/61056 | 12/1999 |
| WO | WO 99/62923 | 12/1999 |
| WO | WO 00/14217 | 3/2000 |
| WO | WO 00/20039 | 4/2000 |
| WO | WO 00/21556 | 4/2000 |
| WO | WO 00/06588 | 10/2000 |
| WO | WO 00/61151 | 10/2000 |
| WO | WO 00/62787 | 10/2000 |
| WO | WO 00/67023 | 11/2000 |
| WO | WO 00/67787 | 11/2000 |
| WO | WO 01/00232 | 1/2001 |
| WO | WO 01/02007 | 1/2001 |
| WO | WO 01/12223 | 2/2001 |
| WO | WO 01/12804 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |
| WO | WO 02/069369 | 9/2002 |

OTHER PUBLICATIONS

Bielorai et al. Successful treatment of invasive aspergillosis in chronic granulomatous disease by granulocyte transfusions followed by peripheral blood stem cell transplantation. Bone Marrow Transplant. Nov. 2000;26(9):1025-8.*

Hamour et al. Visceral leishmaniasis (Kala-azar) in two patients with HIV-1 infection: atypical features and response to therapy. J Infect. Mar. 1998;36(2):217-20. Abstract Only.*

Glaser et al. Animal-associated opportunistic infections among persons infected with the human immunodeficiency virus. Clin Infect Dis. Jan. 1994;18(1):14-24. Review. Abstract Only.*

Davis et al. CpG DNA overcomes hyporesponsiveness to hepatitis B vaccine in orangutans. Vaccine. Mar. 17, 2000;18(18):1920-4.*

Chung et al. HIV/Hepatitis B and C co-infection: pathogenic interactions, natural history and therapy. Antivir Chem Chemother. 2001;12 Suppl 1:73-91. Abstract Only.* de la Rosa et al. Incidence of and risk factors for symptomatic visceral leishmaniasis among human immunodeficiency virus type 1-infected patients from Spain in the era of highly active antiretroviral therapy. J Clin Microbiol. Mar. 2002;40(3):762-7.*

Alvar et al. Leishmania and human immunodeficiency virus coinfection: the first 10 years. Clin Microbiol Rev. Apr. 1997;10(2):298-319.*

Amaral et al., "Leishmania amazonensis: the Asian rhesus macaques (Macaca mulatta) as an experimental model for study of cutaneous leishmaniasis," *Exp. Parasitol.* 82(1):34-44, 1996.

Azzoni et al., "Sustained impairment of IFN-gamma secretion in suppressed HIV-infected patients despite mature NK cell recovery: evidence for a defective reconstitution of innate immunity," *J. Immunol.* 168(11):5764-5770, 2002.

Chehimi, "Persistent decreases in blood plasmacytoid dendritic cell number and function despite effective highly active antiretroviral therapy and increased blood myeloid dendritic cells in HIV-infected individuals," *J. Immunol.* 168(9):4796-4801, 2002.

Gursel, "Sterically stabilized cationic liposomes improve the uptake and immunostimulatory activity of CpG oligonucleotides," *J. Immunol.* 167(6):3324-3328, 2001.

Kenney et al., "Protective immunity using recombinant human IL-12 and alum as adjuvants in a primate model of cutaneous leishmaniasis," *J. Immunol.* 163(8):4481-4488, 1999.

Maddon, "The isolation and nucleotide sequence of a cDNA encoding the T cell surface protein T4: a new member of the immunoglobulin gene family," *Cell* 42(1):93-104, 1985.

Moss and Ledman, "Immunization of the immunocompromised host," *Clinical Focus on Primary Immune Deficiencies* 1(1):1-3, 1998.

Verthelyi et al., "Human peripheral blood cells differentially recognize and respond to two distinct CPG motifs," *J. Immunol.* 166(4):2372-2377, 2001.

Verthelyi et al., "CpG oligodeoxynucleotides as vaccine adjuvants in primates," *J. Immunol.* 168(4):1659-1663, 2002.

Adya, et al., "Expansion of CREB's DNA recognition specificity by Tax results from interaction with Ala-Ala-Arg at positions 282-284 near the conserved DNA-binding domain of CREB". Proc. Natl. Acad. Sci. USA 91(12):5642-5646 (1994).

Agrawal, et al., "Pharmacokinetics of Oligonucleotides". Ciba. Found. Symp. 209:60-78 (1997), abstract only.

Agrawal, et al., "Pharmacokinetics and Bioavailability of Antisense Oligonucleotides Following Oral and Colorectal Adminstration of Experimental Animals". Handb. Exp. Pharmacol.: Antisense Research and Application 131:525-543 (1998).

Agrawal, "Antisense Oligonucleotides: Toward Clinical Trials". Tibtech 14:376-387 (1996).

Agrawal, et al., "In Vivo Pharmacokinetics of Phosphorothloate Oligonucleotides Containing Contiguous Guanosines". Antisense & Nucleic Acid Drug Development 7:245-249 (1997).

Agrawal, et al., "Absorption, Tissue Distribution and In Vivo Stability in Rats of a Hybrid Antisense Oligonucleotide Following Oral Administration". Biochemical Pharmacology 50(4):571-576 (1995).

Agrawal, et al., "Pharmacokinetics of Antisense Oligonucleotides". Clin. Pharmacokinet 28(1):7 (1995).

Agrawal, et al., "Antisense therapeutics: is it as simple as complementary base recognition?". Molecular Med. Today 6(2):72-81 (2000), abstract only.

Agrawal, et al., "Pharmacokinetics, biodistribution, and stability of oligodeoxynucleotide phosphorothioates in mice". Proc. Natl. Acad. Sci. USA 88:7595-7599 (1991).

Agrawal, "Medicinal Chemistry and Therapeutic Potential of CpG DNA". Trends in Molecular Medicine 8(3):114-121 (2002).

Alama, et al., "Antisense Oligonucleotides as Therapeutic Agents". Pharmacol. Res. 36:171-178 (1997).

Anderson, "Human Gene Therapy". Nature 392:25-30 (Apr. 1998).

Anderson, et al., "TH2 and 'TH2-like' cells in allergy and asthma; pharmacological perspectives". TiPS 15:324-332 (1994).

Anfossi, et al., "An oligomer complementary to c-myb-encoded mRNA inhibits proliferation of human myeloid leukemia cell lines". Proc. Natl. Acad. Sci. USA 86:3379-3383 (May 1989).

Angier, "Microbe DNA seen as alien by immune system". New York Times p. C1, 2 pages (1995).

Azad, et al., "Antiviral activity of a phosphorothioate oligonucleotide complementary to RNA of the human cytomegalovirus major immediate-early region". Amtimicrobial Agents and Chemotherapy 37:1945-1954 (1993).

Azuma, "Biochemical and immunological studies on cellular components of tubercle bacilli". Kekkaku 69(9):45-55 (1992).

Ballas, et al., "Induction of NK activity in murine and human cells by CpG motifs in oligodeoxynucleotides and bacterial DNA". J. Immunol. 157(5):1840-1845 (1996).

Banchereau, et al., "Immunobiology of Dendritic Cells". Ann. Rev. Immunol. 18:767-811 (2000).

Banchereau & Steinman, "Dendritic Cells and the Control of Immunity". Nature 392:245-252 (1998).

Barouch, et al., "Control of Viremia and Prevention of Clinical AIDS in Rhesus Monkeys by Cytokine-Augmented DNA Vaccination". Science 290:486-492 (Oct. 2000).

Bauer, et al., "Bacterial CpG-DNA Triggers Activation and Maturation of Human CD11c-, CD123+ Dendritic Cells". J. Immunol. 166:5000-5007 (2001).

Bayever, "Systemic administration of a phosphorothioate oligonucleotide with a sequence complementary to p53 for acute myelogenous leukemia and myelodysplastic syndrome: initial results of a Phase I trial". Antisense Res. Dev. 3:383-390 (1993).

Benimetskaya, et al., "Formation of a G-tetrad and higher order structures correlates with biological activity of the ReIA (NF-κBp65) 'antisense' oligodeoxynucleotide". Nucleic Acids Research 25(13):2648-2656 (1997).

Bennett, et al., "DNA binding to human leukocytes: evidence for a recptor-mediated association, internalization, and degradation of DNA". J. Clin. Invest. 76(6):2182-2190 (1985).

Berg, et al., "Interleukin-10 is a central regulator fo the response to LPS in murine models of endotoxic shock and the Shwartzman reaction but not endotoxin tolerance". J. Clin. Invest. 96(5):2339-2347 (1995).

Biolabs, "1988-1989 Catalog, Random Primer #s 1230, 1601, 1602". ( ).

Bishop, et al., "Intramolecular G-quartet Motifs Confer Nuclease Resistance to a Potent Anti-HIV Oligonucleotide". The Journal of Biological Chemistry 271(10):5698-5703 (Mar. 1996).

Blanchard, et al., "Interferon-γ Induction by Lipopolysaccharide: Dependence of Interleukin 2 and Macrophages". The Journal of Immunology 136(3):963-970 (Feb. 1986).

Blanco, et al., "Induction of Dendritic Cell Differentiation by IFN-α in Systemic Lupus Erythermatosus". Science 294:1540-1543 (2001).

Blaxter, et al., "Genes expressed in Brugia malayi infective third stage larvae". Mol. Biochem. Parasitol. 77:77-93 (1996).

Boggs, et al., "Characterization and modulation of immune stimulation by modified oligonucleotides". Antisense Nucl. Acid Drug Dev. 7(5):461-471 (1997).

Boiarkina, et al., "Dietary supplementals from ground fish meat with DNA for treatment and prophylaxis". Vopr. Pitan 1:29-31 (1998), abstract only.

Branda, et al., "Immune stimulation by an antisense oligomer complementary to the rev gene of HIV-1". Biochem. Pharmacol. 45(10):2037-2043 (1993).

Branda, et al., "Amplification of antibody production by phosphorothioate oligodeoxynucleotides". J. Lab Clin. Med. 128(3):329-338 (1996).

Briskin, et al., "Lipopolysaccharide-unresponsive mutant pre-B-cell lines blocked in NF-kappa B activation". Mol. Cell Bio. 10(1):422-425 (1990).

Burgess, "The antiproliferative activity of c-myb and c-myc antisense oligonucleotides in smooth muscle cells is caused by a nonantisense mechanism". Proc. Natl. Acad. Sci. USA 92:4051-4055 (Apr. 1995).

Calarota, et al., "Immune Responses in Asymptomatic HIV-1 Infected Patients After HIV-DNA Immunization Followed by Highly Active Antiretroviral Threatment". J. Immunol. 163(4):2330-2338 (1999).

Chace, et al., "Regulation of differentiation in CD5+ and conventional B cells". Clin. Immunol. Immunopathol. 68(3):327-332 (1993).

Chang, et al., "The palindromic series I repeats in the simian cytomegalovirus major immediate-early promoter behave as both strong basal enhancers and cyclic AMP response elements". J. Virol. 64(1):264-277 (1990).

Chapuis, et al., "Differentiation of Human Dendritic Cells from Monocytes in vitro". Eur. J. Immunol. 27:431-441 (1997).

Chu, et al., "CpG oligodeoxynucleotides act as adjuvants that switch on T helper 1 (Th1) immunity". J. Exp. Med. 186(10):1623-1631 (1997).

Chun, et al., "Effect of interleukin-2 on the pool of latently infected, resting CD4+ T-cells in HIV-1-infected patients receiving highly active anti-retroviral therapy". Nature Med. 5(6):651-655 (1999).

Chun, et al., "Perspective: Latent reservoirs of HIV: Obstacles to the eradication of virus". Proc. Natl. Acad. Sci. USA 96:10958-10961 (1999).

Cohen, et al., "Exploring How to Get at—and Eradicate—Hidden HIV". Science 279:1854-1855 (1998).

Cohen & Fauci, et al., "HIV/AIDS in 1998—Gaining the Upper Hand?". JAMA 280(1):87-88 (1998).

Cook, et al., "Effect of a Single Ethanol Exposure on HIV Replication in Human Lymphocytes". J. Invest. Med. 45(5):265-271 (1997).

Cooper, et al., "Therapeutic Strategies for HIV Infection—Time to Think Hard". The New England Journal of Medicine 339(18):1319-1321 (1998).

Cowdery, et al., "Bacterial DNA induces NKcells to produce IFN-gamma in vivo and increases the toxici of lipopolysaccharides". J. Immunol. 156(12):4570-4575 (1996).

Crosby, et al., "The early responses gene NGFI-C encodes a zinc finger transcriptional activator and is a member of the GCGGGGGCG (GSG) element-binding protein family". Mol. Cell Bio. 2:3835-3841 (1991).

Crystal, "Transfer of genes to humans: early lessons and obstacles to success". Science 270:404-410 (1995).

Cryz, et al., "Vaccine Delivery System—European Commission COST/STD Initiative Report of the Expert Panel VII". Vaccine 14(7):665-690 (1996).

D'Andrea, et al., "Interleukin 10 (IL-10) inhibits human lymphocyte interferon gamma-production by suppressing natural killer cell stimulatory factor/IL-12 synthesis in accessory cells". J. Exp. Med. 178(3):1041-1048 (1993).

Davey, et al., "HIV-1 and T-Cell dynamics after interruption of highly antiretroviral therapy (HAART) in patients with a history of sustained viral suppression". Proc. Natl. Acad. Sci. USA 96(26):15109-15114 (1999).

Davis, et al., "CpG DNA is a Potent Enhancer of Specific Immunity in Mice Immunized with Recombinant Hepatitis B Surface Antigen". J. Immunol. 160(2):870-876 (1998).

Davis, "Plasmid DNA expression systems for the purpose of immunization". Curr. Opin. Biotechnol. 8(5):635-646 ( Oct. 1997).

Dematos, et al., "Pulsing of Dendritic Cells with Cell Lysates from Either B16 Melanoma or MCA-106 Fibrosarcoma Yields Equally Effective Vaccines Against B16 Tumors in Mice". J. Surg. Oncol. 68:79-91 (1998).

Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).

Dias et al., "Antisense Oligonucleotides: Basic Concepts and Mechanisms," *Mol. Cancer Ther.* 1:317-355, 2002.

Doerfler, et al., "On the Insertion of Foreign DNA into Mammalian Genomes: Mechanism and Consequences". Gene 157(1-2):241-254 (1995), abstract only.

Durham, et al., "Immunotherapy and Allergic Inflammation". Clin. Exp. Allergy 21 Suppl 1:206-210 (1991).

Eck, et al., "Chapter 5: Gene-Based Therapy". Goodman & Gilman's The Pharmacological Basis of Therapeutics 9th ed.:77-101 (1996).

Elkins, et al., "Bacterial DNA containing CpG motifs stimulates lymphocyte-dependent protection of mice against lethal infection with intracellular bacteria". J. Immunol. 162:2291-2298 (1999).

Englisch, et al., "Chemically modified oligonucleotides as probes and inhibitors". Angew. Chem. Int. Ed. Engl. 30:613-629 (1991).

Erb, et al., "Infection of mice with Mycobacterium bovis-badillus Calmette-Guerin (BCG) supresses allergen-induced airway eosinophilia". J. Exp. Med. 184(4):561-569 (1998).

Etlinger, "Carrier sequence selection—one key to successful vaccines". Immunology Today 13(2):52-55 (1992).

Fanslow, et al., "Effect of Nucleotide Restriction and Supplementation on Resistance to Experimental Murine Candidasis". J. Parenter. Enteral. Nutr. 12(1):49-52 Abstract (1988).

Fields, et al., "Murine Dendritic Cells Pulsed With Whole Tumor Lysates Mediate Potent Antitumor Immune Responses in vitro and in vivo". Proc. Natl. Acad. Sci. USA 95:9482-9487 (1998).

Filion, et al., "Major Limitations in the use of Cationic Liposomes for DNA Delivery". Int. J. Pharmaceuticals 162:159-170 (1998).

Fox, "Mechanism of action of hydroxychloroquine as an antirheumatic drug". Chem. Abstracts 120:15, Abstract No. 182630 (1 page) (1994).

Freidag, et al., "CpG oligodeoxynucleotides and interleukin-12 Improve the efficacy of Mycobacterium bovis BCG vaccination in mice challenged with M. tuberculosis". Infect. Immun. 68:2948-2953 (2000).

Gao, et al., "Phosphorothioate oligonucleotides are inhibitors of human DNA polymerases and Rnase H: Implications for antisense technology". Mol. Pharmacol. 41:223-229 (1992).

Garraud, "Regulation of Immunoglobin Production in Hyper-IgE (Job's) Syndrome". J. Allergy Clin. Immunol. 103(2 Pt 1):333-340 (Feb. 1999).

Gluckman, et al., "In Vitro Generation of Human Dendritic Cells and Cell Therapy". Cytokines Cell Mol. Ther. 3:187-196 (1997).

Gramzinski, et al., "Interleukin-12- and gamma interferon-dependent protection against malaria conferred by CpG oligodeoxynucleotide in mice". Infect. Immun. 69(3):1643-1649 (2001).

Gura, "Antisense has growing pains". Science 270:575-576 (1995).

Gursel, et al., "Differential and Competitive Activation of Human Immune Cells by Distinct Classes of CpG Oligodeoxynucleotide". J. Leuko. Biol. 71:813-820 (2002).

Hadden, et al., "Immunopharmacology". JAMA 268(20):2964-2969 (1992).

Hadden, et al., "Immunostimulants". TiPS 141:169-174 (1993).

Halpern, et al., "Bacterial DNA induces murine interferon-gamma production by stimulation of interleukin-12 and tumor necrosis factor-alpha". Cell Immunol. 167(1):72-78 (1996).

Haslett, et al., "Strong Human lmmunodificiency Virus (HIV) Specific CD4+ T Cell Responses in a Cohort of Chronically Infected Patients are Associated with Interruptions in Anti-HIV Chemotherapy". J. Infect. Diseases 181:1264-1272 (2000).

Hatzfeld, "Release of early human hematopoietic progenitors from quiescence by antisense transformin owth factor β1 or Rb oligonucleotides". J. Exp. Med. 174:925-929 (1991).

Havlir, et al., "Maintenance Antiretroviral Therapies in HIV-Infected Subjects with Undetectable Plasma HIV RNA after Triple-Drug Therapy". The New England Journal of Medicine 339(18):1261-1268 (1998).

Hayashi, et al., "Enhancement of innate immunity against Mycobacterium avium infection by immunostimutatory DNA is mediated by indoteamine 2,3-dioxygenase". Infect. Immun. 69:6156-6164 (2001).

Hertl, et al., "Inhibition of Interferon-γ-Induced Intercellular Adhesion Molecule-1 Expression on Human Keratinocytes by Phosphorothioate Antisense Oligodeoxynucleotides is the Consequence of Antisense-Specific and Antisense-Non-Specific Effects". The Journal of Investigative Dermatology 104(5):813-818 (May 1995).

Highfield, "Sepsis: the more, the murkier". Biotechnology 12:828 (1994).

Hoeffler, et al., "Identification of multiple nuclear factors that interact with cyclic adenosine 3',5'-monophosphate response element-binding protein and activating transcription factor-2 by protein-protein interactions". Mol. Endocrinol. 5(2):256-266 (1991).

Honess, et al., "Deviations from Expected Frequencies of CpG Dinucleotides in Herpesvirus DNAs May be Diagnostic of Differences in the States of Their Latent Genomes". J. Gen. Vir. 70(4):837-855 (1989).

Horspool, et al., "Nucleic acid vaccine-induces immune responses require CD28 costimulation and are regulated by CTLA4". J. Immunol. 160:2706-2714 (1998).

Hughes, et al., "Influence of Base Composition on Membrane Binding and Cellular Uptake of 10-mer Phosphorothioate Oligonucleotides in Chinese Hamster Ovary (CHRC5) Cells". Antisense Research and Development 4:211-215 (1994).

Iguchi-Ariga, et al., "CpG methylation of the cAMP-responsive enhancer/promoter sequence TGACGTCA abolishes specific factor binding as well as transcriptional activation". Genes Dev. 3(5):612-619 (1989).

Imami, et al., "Assessment of Type 1 and Type 2 Cytokines in HIV Type 1-Infected Individuals: Impact of Highly Active Antiretroviral Therapy". AIDS Research and Human Retroviruses 15(17)1499-1508 (1999).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).

Ishikawa, et al., "IFN induction and associated changes in splenic leukocyte distribution". J. Immunol. 150(9):3713-3727 (1993).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).

Jakway, et al., "Growth regulation of the B lymphoma cell line WEHI-23 1 by anti-immunoglobulin, lipopolysaccharide, and other bacterial products". J. Immunol. 137(7):2225-2231 (1996).

Jaroszewski, et al., "Cellular uptake of antisense oligonucleotides". Adv. Drug Delivery Rev. 6(3):235-250 (1991).

Jilek, et al., "Antigen-Independent Suppression of the Allergic Immune Response to Bee Venom Phospholipase A2 by DNA Vaccination in CBA/J Mice". J. Immunol. 166:3612-3621 (2001).

Jones, et al., "Synthetic Oligonucleotides Containing CpG Motifs Enhance Immunogenicity of a Peptide Malaria Vaccine in Aotus Monkeys". Vaccine 17:3065-3071 (1999).

Juffermans, et al., "CpG oligodeoxynucleotides enhance host defense during murine tuberculosis". Infect. Immun. 70:147-152 (2002).

Kadowaki, et al., "Distinct CpG DNA and Polyinosinic-Polycytldylic Acid Double Stranded RNA, Respectively, Stimulate CD11c− Type 2 Dendritic Cell Precursoes and CD11c+ Dendritic cells to Produce Type I IFN". J. Immunol. 166:2291-2295 (2001).

Kataoka, et al., "Antitumor activity of synthetic oligonucleotides with sequences from cDNA encodin proteins of Mycobacterium bovis BCG". Jpn. J. Cancer Res. 83:244-247 (1992).

Khaled, et al., "Multiple mechanisms may contribute to the cellular anti-adhesive effects of phosphorothioate oligodeoxynucleotides". Nucleic Acids Research 24(4):737-745 (1996).

Kimura, et al., "Binding of oligoguanylate to scavenger receptors is required for oligonucleotides to augment NK cell activity and induce IFN". J. Biochem 116(5):991-994 (1994).

Kline, et al., "CpG motif oligonucleotides are effective in prevention of eosinophilic inflammation in a murine model of asthma". J. Invest. Med. 44(7):380A (1 page) (1996).

Kline, et al., "CpG oligonucleotides can reverse as well as prevent TH2-mediated inflammation in a murine model of asthma". J. Invest. Med. 45(7):298A (1 page) (1997).

Kline, et al., "Immune redirection by CpG oligonucleotides, Conversion of a Th2 response to a Th1 response in a murine model of asthma". J. Invest. Med. 45(3):282A (1 page) (1997).

Klinman, et al., "Immune recognition of foreign DNA: a cure for bioterrorism?". Immunity 11:123 (1 page) (1999).

Klinman, et al., "Repeated administration of synthetic oligodeoxynucteotides expressing CpG motifs provides tong-term protection against bacterial infection". Infect. Immun. 67:5658-5663 (1999).

Klinman, et al., "CpG motifs present in bacteria DNA rapidly induce lymphocytes to secrete interleukin 6, interleukin 12, and interferon gamma". Proc. Natl. Acad. Sci. USA 93(7):2879-2883 (1996).

Klinman, et al., "Activation of the innate immune system by CpG oligodeoxynucleotides: immunoprotective activity and safety". Springer Semin. Immunopathol. 22:173-183 (2000).

Klinman, et al., "CpG Motids as Immune Adjuvants". Vaccine 17:19-25 (1999).

Kou, et al., "Analysis and Regulation of interferon-gamma production by peripheral blood lymphocytes from patients with bronchial asthma". Arerugi 43(3):483-491 (1994), abstract only.

Krieg, et al., "CpG motifs in bacterial DNA and their immune effect". Annu. Rev. Immunol. 20:709-760 (2002).

Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).

Krieg, et al., "Phosphorothioate oligodeoxynucleotides: antisense or anti-protein?". Antisense Res. Dev. 5:241 (1 page) (1995).

Krieg, et al., "Uptake of oligodeoxyribonucleotides by lymphoid cells is heterogeneous and inducible". Antisense Res. Dev. 1(2):161-171 (1991).

Krieg, et al., "Leukocyte stimulation by oligodeoxynucleotides". Applied Antisense Oligonucleotide Tech. (BOOK):431-448 (1998).

Krieg, et al., "Causing a Commotion in the Blood: Immunotherapy Progresses from Bacteria to Bacterial DNA". Immunology Today 21(10):521-526 (2000).

Krieg, et al., "CpG DNA: A pathogenic factor in systemic lupus erythematosus?". J. Clin. Immunol. 15(6):284-292 (1995).

Krieg, et al, "CpG DNA induces sustained IL-12 expression in vivo and resistance to Listeria monocytogenes challenge". J. Immunol. 161:2428-2434 (1998).

Krieg, et al., "A role for endogenous retroviral sequences in the regulation of lymphocyte activation". J. Immunol. 143(8):2448-2451 (1989).

Krieg, "An innate immune defense mechanism based on the recognition of CpG motifs in microbial DNA". J. Lab. Clin. Med. 128(2):128-133 (Abstract) (1996).

Krieg, et al., "CpG motifs in bacterial DNA trigger direct B-cell activation". Nature 374:546-549 (1995).

Krieg, et al., "Modification of antisense phosphodiester oligodeoxynucleotides by a 5' cholesteryl moiety increases cellular association and improves efficacy". Proc. Natl. Acad. Sci. USA 90:1048-1052 (1993).

Krieg, et al., "The role of CpG dinucleotides in DNA vaccines". Trends in Microbiol. 6:23-27 (1998).

Krieger, et al., "Structures and Functions of Multiligand Lipoprotein Receptors: Macrophage Scavenger Receptors and LDL Receptor-Related Protein (LRP)". Annu. Rev. Biochem 63:601-637 (1994).

Krug, et al., "Identification of CpG Oligonucleotide Sequences with High Induction of IFN-α/β in Plasmacytoid Dendritic Cells". Eur. J. Immunol. 31:2154-2163 (2001).

Krug, et al., "Toll-like Receptor Expression Reveals CpG DNA as a Unigue Microbial Stimulus for Plasmacytoid Dendritic Cells Which Synergizes With CD40 Ligand to Induce High Amounts of IL-12". Eur. J. Immunol. 31:3026-3037 (2001).

Kuchan, et al., "Nucleotides in Infant Nutrition: Effects of Immune Function". Pediatr. Adolesc. Med. Basel. Karger 8:80-94 (1998).

Kulkarni, et al., "Effect of Dietary Nucleotides on Response to Bacterial Infection". J. Parenter. Enteral. Nutr. 10(2):169-171 Abstract (1986).

Kuramoto, et al., "Oligonucleotide sequences required for natural killer cell activation". Jpn. J. Cancer Res. 83:1128-1131 (1992).

Lagrange, et al., "Immune Responses Directed Against Infectious and Parasitic Agents". Immunology (BOOK—ISBN:0471017604) (Chapter of Book; Ed—Jean-François Bach): (1978).

Lang, et al., "Guanosine-rich oligodeoxynucleotides induce proliferation of macrophage progenitors in cultures of murine bone marrow cells". Eur. J. Immunol. 29:3496-3506 (1999).

Lapatschek, et al., "Activation of Macrophages and B Lymphocytes by an Oligodeoxynucleotide Derived from an Acutely Pathogenic Simian Immunodeficiency Virus". Antisense Nucleic Acid Drug Dev. 8(5):357-370 (Oct. 1998).

Ledergerber, et al., "Clinical Progression and Virological Failure on Highly Active Antiretroviral Therapy in HIV-1 Patients: a Prospective Cohort Study". The Lancet 353:863-868 (1999).

Lederman, et al., "Polydeooxyguanine Motifs in a 12-mer Phosphorothioate Oligodeooxynucleotide Augment Binding to the v3 Loop of the HIV-1 gp120 and Potency of HIV-1 Inhibition Independently of G-Tetrad Formation". Antisense & Nucleic Acid Drug Development 6:281-289 (1996).

Lee, et al., "An Oligonucleotide Blocks Interferon-γ Signal Transduction". Transplantation 62(9):1297-1301 (1996).

Leibson, et al., "Role of γ-interferon in antibody-producing responses". Nature 309:799-801 (1984).

Leonard, et al., "Conformation of guanine 8-oxoadenine base pairs in the crystal structure of d(CGCGAATT(O8A)GCG)". Biochemistry 31(36):8415-8420 (1992).

Li, et al., "Long-Lasting Recovery in CDR T-Cell Function and Viral-Load Reduction After Highly Active Antiretroviral Therapy in Advanced HIV-1 Disease". The Lancet 351:1682-1686 (1998).

Liang, et al., "Activation of Human B Cells by Phosphorothioate Oligodeoxynucleotides". J. Clin. Invest. 98:1119-1129 (1996).

Lipford, et al., "CpG-containing synthetic oligonucleotides promote B and cytotoxic T cell responses to protein antigen: a new class of vaccine adjuvants". Eur. J. Immunol. 27(9):2340-2344 (1997).

Lipford, et al., "Immunostimulatory DNA: sequence-dependent production of potentially harmful or useful cytokines". Eur. J. Immunol. 27(12):3420-3426 (1997).

Lönnberg, et al., "Towards Genomic Drug Therapy with Antisense Oligonucleotides". Ann. Med. 28:511-522 (1996).

Macaya, et al., "Thrombin-binding DNA aptamer forms a unimolecular quadruplex structure in solution". Proc. Natl. Acad. Sci. USA 90:3745-3749 (Apr. 1993).

MacFarlane, et al., "Antagonism of immunostimulatory CpG-oligodeoxynucleotides by quinacrine, chloroquine, and structurally related compounds". J. Immunol. 160(3):1122-1131 (1998).

Maltese, et al., "Sequence context of antisense RelA/NF-kB phohphorothioates determines specificity". Nucleic Acids Research 23(7):1146-1151 (1995).

Manzel, et al., "Lack of Immune Stimulation by Immobilized CpG-oligonucletide". Antisense & Nucleic Acid Drug Development 9(5):459-464 (1999).

Mastrangelo, et al., "Gene therapy for human cancer: an essay for clinicians". Seminars Oncology 23(1):4-21 (1996).

Matson, et al., "Nonspecific suppression of [3H]thymidine incorporation by control oligonucleotides". Antisense Res. Dev. 2(4):325-330 (1992).

McCluskie, et al., "Cutting Edge: CpG DNA Is a Potent Enhancer of Systemic and Mucosal Immune Responses Against Hepatitis B Surface Antigen with Intranasal Administration to Mice". J. Immun. 161:4463-4465 (1998).

McCluskie, et al., "Route and Method of DNA Vaccine Influence Immune Responses in Mice and Non-Human Primates". Molecular Med. 5(5):287-300 (1999).

McIntyre, et al., "A sense phosphorothioate oligonucleotide directed to the initiation codon of transcription factor NF-kappa B p65 causes sequence-specific immune stimulation". Antisense Res. Dev. 3(4):309-322 (1993).

McKenzie, "Nucleic Acid Vaccines". Immunologic Res. 24(3):225-244 (2001).

Merad, et al., "In vivo Manipulation of Dendritic Cells to Induce Therapeutic Immunity". Blood 99(5):1676-1682 (2002).

Messina, et al., "Stimulation of in vitro murine lymphocyte proliferation by bacterial DNA". Cell Immunol. 147(6):1759-1764 (1991).

Messina, et al., "The influence of DNA structure on the in vitro stimulation of murine lymphocytes by natural and synthetic polynucleotide antigens". J. Immunol. 147:148-157 (1993).

Mojcik, et al., "Administration of a phosphorothioate oligonucleotide antisense murine endogenous retroviral MCF env causes immune effect in vivo in a sequence-specific manner". Clin. Immunol. Immunopathol. 67(2):130-136 (1993).

Mottram, et al., "A novel CDC2-related protein kinase from leishmania mexicana, LmmCRK1, is post-translationally regulated during the life cycle". J. Biol. Chem. 268(28):21044-21052 (1993).

Nyce, et al., "DNA antisense therapy for asthma in an animal model". Nature 385:721-725 (1997).

Oberbauer, "Not nonsense but antisense—Applications of Antisense Oligonucleotides in Different Fields of Medicine". Wein Klin Wochenschr 109:40-46 (1997).

Ogg, et al., "Quantitation of HIV-1-Specific Cytotoxic T-Lymphocytes and Plasma Load of Viral RNA". Science 279:2103-2106 (1998).

Okada, et al., "Bone Marrow-Derived Dendritic Cells Pulsed With a Tumor-Specific Peptide Elicit Effective Anti-Tumor Immunity Against Intracranial Neoplasms". Int. J. Cancer 78:196-201 (1998).

Palucka, et al., "Dendritic Cells as the Terminal Stage of Monocyte Differentiation". J. Immunol. 160:4587-4595 (1999).

Papasavvas, et al., "Enhancement of Human Immunodeficiency Virus Type I-Specific CD4 and CD8 T Cell Responses in Chronically Infected Persons after Temporary Treatement Interruption". J. Infect. Diseases 182:766-775 (2000).

Pialoux, et al., "A Randomized Trial of Three Maintenance Regimens Given After Three Months of Induction Therapy with Zidovudine, Lamivudine, and Indinavie in Previously Untreated HIV-1-Infected Patients". The New England Journal of Medicine 339(18):1269-1276 (1998).

Piscitelli, "Immune-Based Therapies for Treatment of HIV Infection". The Annals of Pharmacotherapy 30:62-76 (1996).

Pisetsky, et al., "Immunological Properties of Bacterial DNA". Ann. NY Acad. Sci. 772:152-163 (1995).

Pisetsky, "Immunological consequences of nucleic acid therapy". Antisense Res. Dev. 5:219- 225 (1995).

Pisetsky, "The immunological properties of DNA". J. Immunol. 156:421-423 (1996).

Pisetsky, et al., "Stimulation of murine lymphocyte proliferation by a phosphorothioate oligonucleotide with antisense activity for hepes simplex virus". Life Science 54:101-107 (1994).

Pisetsky, "Stimulation of in vitro proliferation of murine lymphocytes by synthetic oligodeoxyucleotides". Molecular Biol. Reports 18:217-221 (1993).
Plenat, "Animal models of antisense oligonucleotides: lessons for use in humans". J. Mol. Med. Today 2(6):250-257 (1996).
Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide". Antimicrobial Agents and Chemotherapy 43(11):2689-2696 (Nov. 1999).
Quddus, et al., "Treating activated CD4+ T cells with either of two distinct DNA methyltransferase inhibitors, 5-azacytidine or procaniamlde, is sufficient to cause a lupus-like disease in syngeneic mice". J. Clin. Invest. 92(1):38-53 (1993).
Ramanathan, et al., "Characterization of the Oligodeoxynucleotide-mediated Inhibition of Interferon-γ-induced Major Histocompatibility Complex Class I and Intercellular Adhesion Molecule-1". The Journal of Biological Chemistry 269(40):24564-24574 (Oct. 1994).
Ramanathan, et al., "Inhibition of Interferon-γ-Induced Major Histocompatibility Complex Class I Expression by Certain Oligodeoxynucleotides". Transplantation 57(4):612-615 (Feb. 1994).
Raz, "Deviation of the Allergic IgE to an IgG Response by Gene Immunotherapy". Int. Rev. Immunol. 18(3):271-289 (1999).
Raz, et al., "Preferential Induction of a Th1 Immune Response and Inhibition of Specific IgE Antibody Formation by Plasmid DNA Immunization". Proc. Natl. Acad. Sci. USA 93:5141-5145 (1996).
Raz, et al., "Intradermal gene immunization: the possible role of DNA uptake in the induction of cellular immunity to viruses". Proc. Natl. Acad. Sci. USA 91:9519-9523 (1994).
Ricci, et al., "T cells, cytokines, IgE and allergic airways inflammation". J. Invest. Allergol Clin. Immunol. 4(5):214-220 (1994).
Rojanasakul, "Antisense oligonucleotide therapeutics: drug delivery and targeting". Drug Delivery Reviews 18:115-131 (1996).
Roman, et al., "Immunostimulatory DNA sequences function as T helper-1-promoting aduvants". Nature Med. 3(8):849-854 (1997).
Rosenberg, et al., "Immune Control of HIV-1 After Early Treatment of Acute Infection". Nature 407:523-526 (2000).
Rosenberg, et al., "Vigorous HIV-1-Specific CD4+ T-Cell Responses Associated with Control of Viremia". Science 278:1447-1450 (1997).
Ruiz, et al., "Structured Treatment Interruption in Chronically HIV-1 Infected Patients After Long-Term Viral Suppression". AIDS 14:397-403 (2000).
Santini, et al., "Type I Interferon as a Powerful Adjuvant for Monocyte-derived Dendritic Cell Development and Activity In Vitro and in Hu-PBL-SCID Mice". J. Exp. Med. 191:1777-1788 (2000).
Sato, et al., "Immunostimulatory DNA sequences necessary for effective intradermal gene immunization". Science 273:352-354 (1996).
Scanlon, et al., "Oligonucleotide-mediated Modulation of Mammalian Gene Expression". FASEB J. 9:1288-1295 (1995).
Schnell, et al., "Identification and characterization of a *Saccharomyces cerevisiae* gene (PAR 1) conferring resistance to iron chelators". Eur. J. Biochem. 200:487-493 (1991).
Schoofs, "Small Steps—A Limited Experiment Opens New Approach in Fight Against HIV". Wall Street Journal (Sep. 28, 2000).
Schubert, et al., "Ingested Foreign (phage M13) DNA Survives Transiently in the Gastrointestinal Tract and Enters the Bloodstream of Mice". Mol. Gen. Genet. 242:495-504 (1994).
Schwartz, et al., "Endotoxin responsiveness and grain dust-induced inflammation in the lower respiratory tract". Am. J. Physiol. 267(5):609-617 (1994).
Schwartz, et al., "The role of endotoxin in grain dust-induced lung disease". Am. J. Respir. Crit. Care Med. 152(2):603-608 (1995).
Schwartz, et al., "CpG motifs in bacterial DNA cause inflammation in the lower respiratory tract". J. Clin. Invest. 100(1):68-73 (1997).
Sedegah, et al., "Intertukin 12 induction of interferon g-dependent protection against malaria". Proc. Natl. Acad. Sci. USA 91:10700-10792 (1994).
Sethi, et al., "Postexposure prophytaxis against prion disease with a stimulator of innate immunity". Lancet 360:229-230 (2002).
Shafer, et al., "Highly Active Antiretroviral Therapy (HAART) for the Treatment of Infection With Human Immunodeficiency Virus Type 1". Biomed. & Pharmachther. 53:73-86 (1999).
Shirakawa, et al., "The inverse association between tuberculin responses and atopic disorder". Science 275(5296):77-79 (1997).
Sidman, et al., "γ-Interferon is one of several direct B cell-maturing lymphokines". Nature 309:801-804 (1984).
Sparwasser, et al., "Macrophages sense pathogens via DNA motifs: induction of tumor necrosis factor-alpha-mediated shock". Eur. J. Immunol. 27(7):1671-1679 (1997).
Sparwasser, et al., "Bacterial DNA and immunostimulatory CpG oligonuceotides trigger maturation and activation of murine dendritic cells". Eur. J. Immunol. 28:2045-2054 (1998).
Spiegelberg, et al., "Recognition of T Cell Epitopes and Lymphokine Secretion by Rye Grass Allergen Lolium perenne I-Specific Human T Cell Clones". J. of Immunology 152:4706-4711 (1994).
Stacey, et al., "Immunostimulatory DNA as an adjuvant in vaccination against Leishmania major". Infect. Immun. 67:3719-3726 (1999).
Stein, et al., "Oligodeoxynucleotides as inhibitors of gene expression: a review". Cancer Res. 48:2659-2668 (1998).
Stull, et al., "Antigene, ribozyme, and aptamer nucleic acid drugs: progress and prospects". Pharm. Res. 12(4):465-483 (1995).
Su, et al., "Vaccination against Chlamydial Genital Tract Infection after Immunization with Dendritic Cells Pulsed Ex Vivo with Nonviable Chlamydiae". J. Exp. Med. 188:809-818 (1998).
Subramanian, et al., "Theoretical considerations on the 'spine of hydration' in the minor groove of d(CGCGAATTCGCG) d(CGGCT-TAAGCGC): Monte Carlo computer simulation". Proc. Natl. Acad. Sci. USA 85:1836-1840 (1988).
Syme, et al., "Generation of Dendritic Cells ex vivo: Differences in Steady State versus Mobilized Blood from Patients with Breast Cancer, with Lymphoma, and from Normal Donors". J. Hemather. Stem Cell Res. 10:621-630 (2001).
Tanaka, et al., "An antisense oligonucleotide complementary to a sequence in I gamma 2b increases gamma 2b germhine transcripts, stimulates B cell DNA synthesis and inhibits immunoglobulin secretion". J. Exp. Med. 175:597-607 (1992).
Tarte, et al., "Extensive characterization of dendritic cells generated in serum-free conditions: regulation of soluble antigen uptake, apoptotic tumor cell phagocytosis, chemotaxis and T cell activation during maturation in vitro". Leukemia 14:2182-2192 (2000).
Thorne, "Experimental grain dust atmospheres generated by wet and dry aerosolization techniques". Am. J. Ind. Med. 25(1):109-112 (1994).
Tighe, et al., "Conjunction of Protein to Immunostimulatory DNA results in a Rapid Long-Lasting and Potent Induction of Cell-Mediated and Humoral Immunity". Eur. J. Immunol. 30:1939-1947 (2000).
Tokunaga, et al., "A synthetic single-stranded DNA, poly(dG, dC), induces interferon-α/β and -γ, augments natural killer activity and suppresses tumor growth". Jpn. J. Cancer Res. 79:682-686 (1988).
Tokunaga, et al., "Synthetic oligonucleotides with particular base sequences from the cDNA encoding proteins of Mycobacterium bovis BCG induce interferons and activate natural killer cells". Microbiol. Immunol. 36(1):55-66 (1992).
Uhlmann, et al., "Antisense oligonucleotides: a new therapeutic principle". Chem. Rev. 90:543-584 (1990).
Verdijk, et al., "Polyriboinosinic Polyribocytidylic Acid (Poly(I:C)) Induces Stable Maturation of Functionally Active Human Dendritic Cells". J. Immunol. 163:57-61 (1999).
Verma, et al., "Gene therapy—promises, problems and prospects". Nature 389:239-242 (Sep.1997).
Vil'Ner, "Effect of Amphotericin B on the interferonogenic activity of poly(G).poly (C) and poly(G,I).poly(C) in mice and their resistance to infection by the tick-borne encephalitis virus". Antibiotiki 27(11):827-830 (Nov. 1982), abstract only.
Vil'Ner, et al., "Effect of virazole on the antiviral activity of poly(G) X poly © and other polyribonucleotide interferongens". Antibiotiki 29(6):450-453 (1984), abstract only.
Vil'Ner, et al., "Evaluation of the size of the continuous poly(G) site necessary for the biological activity of the poly(G).poly(C) complex". Vopr Virusol 30(3):337-340 (1985), abstract only.

Vil'Ner, "Effect of the size of the continuous poly(G) site in poly(G,A).poly(C) complexes on their interferon-inducing activity and their capacity to stimulate the development of the immunity". Vopr Virusol 31(6):697-700 (1986), abstract only.

Vil'Ner, et al., "Dependence of the antiviral activity of the poly(G).poly(C) complex on the size of the continuous poly(C) segments". Vopr Virusol 33(3):331-335 (1988), abstract only.

Wagner, "Bacterial CpG DNA Activates Immune Cells to Signal Infectious Danger". Adv. Immunol. 73:329-368 (1999).

Wagner, "Gene inhibition using antisense oligodeoxynucleotides". Nature 372:333-335 (1994).

Walker, et al., "Activated T Cells and Cytokines in Bronchoalveolar Lavages from Patients with Various Lung Diseases Associated with Eosinophilia". Am. J. Respir. Crit. Care Med. 150:1038 1048 (1994).

Walker, et al., "Immunostimulatory oligodeoxynucleotides promote protective immunity and provide systemic therapy for leishmaniasis via IL-12- and IFN-g-dependent mechanisms". Proc. Natl. Acad. Sci. USA 96:6970-6975 (1999).

Wallace, et al., "Oligonucleotide probes for the screening of recombinant DNA libraries". Methods Enzymol. 152:432-442 (1987).

Weiner, "The immunobiology and clinical potential of immunostimulatory CpG oligodeoxynucleotides". Leukocyte Bio. 68:455-463 (2000).

Weiner, et al., "Immunostimulatory oligodeoxynucleotides containing the CpG motif are effective as immune adjuvants in tumor antigen immunization". Proc. Natl. Acad. Sci. USA 94:10833-10837 (1997).

Weiss, "Upping the antisense ante: scientists bet on profits from reverse genetics". Science 139:108-109 (1991).

Whalen, et al., "DNA-Mediated Immunization to the Helatitis B Surface Antigen: Activation and Entrainment of the Immune Response". Ann. NY Acad. Sci. 772:64-76 (1995).

Whalen, "DNA vaccines for emerging infection diseases: what if?". Emerg. Infect. Dis. 2(3):168-175 (1996).

Wloch, et al., "The influence of DNA sequence on the immunostimulatory properties of plasmid DNA vectors". Hum. Gene Ther. 9(10):1439-1447 (Jul. 1998).

Woolridge, et al., "Immunostimulatory oligodeoxynucleotides containing CpG motifs enhance the efficacy of monoclonal antibody therapy of lymphoma". Blood 89:2994-2998 (1997).

Wu, et al., "Receptor-mediated gene delivery and expression in vivo". J. Biol. Chem. 263:14621-14624 (1988).

Wu-Pong, "Oligonucleotides: opportunities for drug therapy and research". Pharmaceutical Tech. 18:102-114 (1994).

Wyatt, et al., "Combinatorially selected guanosine-quartet structure is a potent Inhibitor of human immunodeficiency virus envelope-mediated cell fusion". Proc. Natl. Acad. Sci. USA 91:1356-1360 (Feb. 1994).

Yamamoto, et al., "Ability of oligonucleotides with certain palindromes to induce interferon production and augment natural killer cell activity is associated with their base length". Antisense Res. Dev. 4:119-123 (1994).

Yamamoto, "Unique palindromic sequences in synthetic oligonucleotides are required to induce inf and augment INF-mediated natural killer activity". J. Immunol. 148(12):4072-4076 (1992).

Yamamoto, et al., "In vitro augmentation of natural killer cell activity and production of interferon-alpha/beta and -gamma with deoxyribonucleic acid fraction from Mycobacterium bovis BCG". Jpn. J. Cancer Res. 79:866-873 (1988).

Yamamoto, et al., "Synthetic oligonucleotides with certain palindromes stimulate interferon production of human peripheral blood lymphocytes in vitro". Jpn. J. Cancer Res. 85:775-779 (1994).

Yamamoto, et al., "Mode of action of oligonucleotide fraction extracted from Mycobacterium bovis BeG". Kekkaku 69(9):29-32 (1994).

Yamamoto, et al., "DNA from bacteria, but not vetebrates, induces interferons, activates natural killer cells, and inhibits tumor growth". Microbiol. Immunol. 36(9):983-997 (1992).

Yamamoto, et al., "Lipofection of synthetic oligodeoxyribonucleotide having a palindromic sequence AACGTT to murine splenocytes enhances interferon production and natural killer activity". Microbiol. Immunol. 38(10):831-836 (1994).

Yaswen, et al., "Effects of Sequence of Thioated Oligonucleotides on Cultured Human Mammary Epithelial Cells". Antisense Research and Development 3:67-77 (1993).

Yew, et al., "Contribution of Plasmid DNA to Inflammation in the Lung After Administration of Cationic Lipid: pDNA Complexes". Hum. Gene Ther. 10(2):223-234 (1999).

Yi, et al, "IFN-γ promotes IL-6 and IgM secretion in response to CpG motifs in bacterial DNA and oligonucleotides". J. Immunol. 156:558-564 (1996).

Yi, et al., "Rapid immune activation by CpG motifs in bacterial DNA". J. Immunol. 157:5394-5402 (1996).

Zelphati, et al., "Inhibition of HIV-1 Replication in Cultured Cells with Antisense Oligonucleotides Encapsulated in Immunoliposomes". Antisense Res: Dev. 3:323 (1993).

Zhang, et al., "Antigen- and Isotype-Specific Immune Responses to a Recombinant Antigen-Allergen Chimeric (RAAC) Protein". J. Immunol. 151:791-799 (1993).

Zhao, et al, "Comparison of cellular binding and uptake of antisense phosphodiester, phosphorothioate, and mixed phosphorothioate and methylphosphonate oligonucleotides". Antisense Res. Dev. 3(1):53-66 (1993).

Zhao, et al., "Stage-specific oligonucleotide uptake in murine bone marrow B-cell precursors". Blood 84(11):3660-3666 (1994).

Zheng, et al., "Contribution of Vascular Endothelial Growth Factor in the Neovascularization Process During the Pathogenesis of Herpetic Stromal Keratitis". J. Vriol. 75(20):9828-9835 (2001).

Zhu, et al., "Macaque blood-derived antigen-presenting cells elicit SIV-specific immune responses". J. Med. Primatol 29:182-192 (2000).

Zimmermann, et al., "CpG oligodeoxynucleotides trigger protective and curative Th1 responses in lethal murine leishmaniasis". J. Immunol. 160:3627-3630 (1998).

U.S. Doc. No. 6,008,200, Dec. 28, 1999, (withdrawn).

* cited by examiner

SEQUENCE LISTING

```
<160> NUMBER OF SEQ ID NOS: 181

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 1
nntgcatcga tgcagggggg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 2
nntgcaccgg tgcagggggg                                               20

<210> SEQ ID NO 3
<211> LENGTH: 20
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 3
nntgcgtcga cgcagggggg                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 4
nntgcgtcga tgcagggggg                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 5
nntgcgccgg cgcagggggg                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 6
nntgcgccga tgcagggggg                                          20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 7
nntgcatcga cgcagggggg                                          20

<210> SEQ ID NO 8
<211> LENGTH: 20
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t, or no nucleotide

<400> SEQUENCE: 8
nntgcgtcgg tgcaggggggg                                              20

<210> SEQ ID NO 9
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 9 atcgat                                                              6

<210> SEQ ID NO 10
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 10 accggt                                                              6

<210> SEQ ID NO 11
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 11 atcgac                                                              6

<210> SEQ ID NO 12
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 12 accgat                                                              6

<210> SEQ ID NO 13
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 13 gtcgac                                                              6

<210> SEQ ID NO 14
<211> LENGTH: 6
<212> TYPE: DNA
<213> ORGANISM: Artificial Sequence
<220> FEATURE:
<223> OTHER INFORMATION: Synthetic oligonucleotide
```

<400> SEQUENCE: 14 gccggc                                                                6

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ggtgcatcga tacagggggg                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
ggtgcgtcga tgcagggggg                                                20

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t

<400> SEQUENCE: 17
gtctgcgtca tntggtgcat tc                                             22

<210> SEQ ID NO 18
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 18
cactagntgt ctctgcacta tntgttttg                                      29

<210> SEQ ID NO 19
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t -continued

```
<400> SEQUENCE: 19
cttcntcagt ntgtttcact ttctcttctg cg                                    32

<210> SEQ ID NO 20
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(10)
<223> OTHER INFORMATION: n is a, c, g, or t

<400> SEQUENCE: 20 nnntcnnnnn                                                             10

<210> SEQ ID NO 21
<211> LENGTH: 6
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t

<400> SEQUENCE: 21 rycnry                                                                  6

<210> SEQ ID NO 22
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 22
nnnrycgryn nnggggg                                                     16

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 23
nnnrycgryn nnngggg                                                     17
```

```
<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 24
nnnrycgryn nnnngggg                                                 18

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 25
nnnrycgryn nnnnnggg                                                 19

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 26
nnnrycgryn nnnnnnggg                                                20

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 27
nnnrycgryn nnnnnnnggg g                                             21
```

```
<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 28
nnnrycgryn nnnnnnnngg gg                                              22

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 29
nnnrycgryn nnnnnnnnng ggg                                             23

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 30
nnnrycgryn nnnnnnnnnn gggg                                            24

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 31
nnnrycgryn nnnnnnnnnn ngggg                                           25
```

```
<210> SEQ ID NO 32
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 32
nnnrycgryn nnnnnnnnnn nnggqq                                          26

<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 33
nnnrycgryn nnggggg                                                    17

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 34
nnnrycgryn nnnggggg                                                   18

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 35
nnnrycgryn nnnnggggg                                                  19
```

```
<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 36
nnnrycgryn nnnnnggggg                                              20

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 37
nnnrycgryn nnnnnngggg g                                            21

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 38
nnnrycgryn nnnnnnnggg gg                                           22

<210> SEQ ID NO 39
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 39
nnnrycgryn nnnnnnnngg ggg                                          23
```

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 40
nnnrycgryn nnnnnnnnng gggg                                              24

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 41
nnnrycgryn nnnnnnnnnn ggggg                                             25

<210> SEQ ID NO 42
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 42
nnnrycgryn nnnnnnnnnn nggggg                                            26

<210> SEQ ID NO 43
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 43
nnnrycgryn nnnnnnnnnn nnggggg                                           27

```
<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 44
nnnrycgryn nngggggg                                          18

<210> SEQ ID NO 45
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 45
nnnrycgryn nnnggggggg                                        19

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 46
nnnrycgryn nnnngggggg                                        20

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 47
nnnrycgryn nnnnnggggg g                                      21
```

```
<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 48
nnnrycgryn nnnnnngggg gg                                              22

<210> SEQ ID NO 49
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 49
nnnrycgryn nnnnnnnggg ggg                                             23

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 50
nnnrycgryn nnnnnnnngg gggg                                            24

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 51
nnnrycgryn nnnnnnnnng ggggg                                           25
```

```
<210> SEQ ID NO 52
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 52
nnnrycgryn nnnnnnnnnn gggggg                                       26

<210> SEQ ID NO 53
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 53
nnnrycgryn nnnnnnnnnn nggggggg                                     27

<210> SEQ ID NO 54
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 54
nnnrycgryn nnnnnnnnnn nnggggggg                                    28

<210> SEQ ID NO 55
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 55
nnnrycgryn nngggggggg                                              19
```

```
<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 56
nnnrycgryn nnnggggggg                                               20

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 57
nnnrycgryn nnnngggggg g                                             21

<210> SEQ ID NO 58
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 58
nnnrycgryn nnnnnggggg gg                                            22

<210> SEQ ID NO 59
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 59
nnnrycgryn nnnnnngggg ggg                                           23
```

```
<210> SEQ ID NO 60
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 60
nnnrycgryn nnnnnnnggg gggg                                         24

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 61
nnnrycgryn nnnnnnnngg ggggg                                        25

<210> SEQ ID NO 62
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 62
nnnrycgryn nnnnnnnnng gggggg                                       26

<210> SEQ ID NO 63
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 63
nnnrycgryn nnnnnnnnnn ggggggg                                      27
```

```
<210> SEQ ID NO 64
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 64
nnnrycgryn nnnnnnnnnn ngggggggg                                28

<210> SEQ ID NO 65
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 65
nnnrycgryn nnnnnnnnnn nngggggggg                               29

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 66
nnnrycgryn nngggggggg                                          20

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 67
nnnrycgryn nnngggggggg g                                       21
```

```
<210> SEQ ID NO 68
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 68
nnnrycgryn nnnngggggg gg                                              22

<210> SEQ ID NO 69
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 69
nnnrycgryn nnnnnggggg ggg                                             23

<210> SEQ ID NO 70
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 70
nnnrycgryn nnnnnngggg gggg                                            24

<210> SEQ ID NO 71
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 71
nnnrycgryn nnnnnnnggg ggggg                                           25
```

```
<210> SEQ ID NO 72
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 72
nnnrycgryn nnnnnnnngg gggggg                                    26

<210> SEQ ID NO 73
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 73
nnnrycgryn nnnnnnnnng ggggggg                                   27

<210> SEQ ID NO 74
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 74
nnnrycgryn nnnnnnnnnn ggggggg                                   28

<210> SEQ ID NO 75
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 75
nnnrycgryn nnnnnnnnnn nggggggg                                  29
```

```
<210> SEQ ID NO 76
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 76
nnnrycgryn nnnnnnnnnn nnggggggggg                                         30

<210> SEQ ID NO 77
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 77
nnnrycgryn nnggggggggg g                                                  21

<210> SEQ ID NO 78
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 78
nnnrycgryn nnnggggggg gg                                                  22

<210> SEQ ID NO 79
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 79
nnnrycgryn nnnnggggg ggg                                                  23
```

```
<210> SEQ ID NO 80
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 80
nnnrycgryn nnnngggg gggg                                                   24

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 81
nnnrycgryn nnnnnnggg ggggg                                                 25

<210> SEQ ID NO 82
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 82
nnnrycgryn nnnnnnnggg gggggg                                               26

<210> SEQ ID NO 83
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 83
nnnrycgryn nnnnnnnngg ggggggg                                              27
```

```
<210> SEQ ID NO 84
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 84
nnnrycgryn nnnnnnnnng ggggggggg                              28

<210> SEQ ID NO 85
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 85
nnnrycgryn nnnnnnnnnn ggggggggg                              29

<210> SEQ ID NO 86
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 86
nnnrycgryn nnnnnnnnnn nggggggggg                             30

<210> SEQ ID NO 87
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 87
nnnrycgryn nnnnnnnnnn nnggggggggg g                          31
```

```
<210> SEQ ID NO 88
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 88
nnnrycgryn nngggggggg gg                                              22

<210> SEQ ID NO 89
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 89
nnnrycgryn nnnggggggg ggg                                             23

<210> SEQ ID NO 90
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 90
nnnrycgryn nnnngggggg gggg                                            24

<210> SEQ ID NO 91
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 91
nnnrycgryn nnnnnggggg ggggg                                           25
```

```
<210> SEQ ID NO 92
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 92
nnnrycgryn nnnnnnggggg gggggg                                          26

<210> SEQ ID NO 93
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 93
nnnrycgryn nnnnnnnggg ggggggg                                          27

<210> SEQ ID NO 94
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 94
nnnrycgryn nnnnnnnngg gggggggg                                         28

<210> SEQ ID NO 95
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 95
nnnrycgryn nnnnnnnnng ggggggggg                                        29
```

```
<210> SEQ ID NO 96
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 96
nnnrycgryn nnnnnnnnnn gggggggggg                                     30

<210> SEQ ID NO 97
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 97
nnnrycgryn nnnnnnnnnn ngggggggggg g                                  31

<210> SEQ ID NO 98
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (13)..(22)
<223> OTHER INFORMATION: n is a, c, g, t, or no nucleotide
<220> FEATURE:
<221> NAME/KEY: misc_feature
<222> LOCATION: (23)..(28)
<223> OTHER INFORMATION: n is g or no nucleotide

<400> SEQUENCE: 98
nnnrycgryn nnnnnnnnnn nnnnnnnngg gg                                  32

<210> SEQ ID NO 99
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(14)
<223> OTHER INFORMATION: n is a, c, g, or t

<400> SEQUENCE: 99
ggnnnrycgr ynnngggg                                              18

<210> SEQ ID NO 100
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 100
ggnnnrycgr ynnnngggg                                             19

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 101
ggnnnrycgr ynnnnngggg                                            20

<210> SEQ ID NO 102
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 102
ggnnnrycgr ynnnnnnggg g                                          21

<210> SEQ ID NO 103
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(18)
<223> OTHER INFORMATION: n is a, c, g, or t

<400> SEQUENCE: 103
ggnnnrycgr ynnnnnnngg gg                                              22

<210> SEQ ID NO 104
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 104
ggnnnrycgr ynnnnnnnng ggg                                             23

<210> SEQ ID NO 105
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 105
ggnnnrycgr ynnnnnnnnn gggg                                            24

<210> SEQ ID NO 106
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 106
ggnnnrycgr ynnnnnnnnn ngggg                                           25

<210> SEQ ID NO 107
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(22)
<223> OTHER INFORMATION: n is a, c, g, or t

<400> SEQUENCE: 107
ggnnnrycgr ynnnnnnnnn nnggggg                                             26

<210> SEQ ID NO 108
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 108
ggnnnrycgr ynnnnnnnnn nnngggg                                             27

<210> SEQ ID NO 109
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 109
ggnnnrycgr ynnnnnnnnn nnnngggg                                            28

<210> SEQ ID NO 110
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 110
ggnnnrycgr ynnnggggg                                                      19

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(15)
<223> OTHER INFORMATION: n is a, c, g, or t

<400> SEQUENCE: 111
ggnnnrycgr ynnnnggggg                                                    20

<210> SEQ ID NO 112
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 112
ggnnnrycgr ynnnnnggggg g                                                 21

<210> SEQ ID NO 113
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 113
ggnnnrycgr ynnnnnnggg gg                                                 22

<210> SEQ ID NO 114
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 114
ggnnnrycgr ynnnnnnngg ggg                                                23

<210> SEQ ID NO 115
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(19)
<223> OTHER INFORMATION: n is a, c, g, or t

<400> SEQUENCE: 115
ggnnnrycgr ynnnnnnnng gggg                                          24

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 116
ggnnnrycgr ynnnnnnnnn ggggg                                         25

<210> SEQ ID NO 117
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 117
ggnnnrycgr ynnnnnnnnn nggggg                                        26

<210> SEQ ID NO 118
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 118
ggnnnrycgr ynnnnnnnnn nnggggg                                       27

<210> SEQ ID NO 119
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(23)
<223> OTHER INFORMATION: n is a, c, g, or t

<400> SEQUENCE: 119
ggnnnrycgr ynnnnnnnnn nnnggggg                                              28

<210> SEQ ID NO 120
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 120
ggnnnrycgr ynnnnnnnnn nnnnggggg                                             29

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 121
ggnnnrycgr ynnnggggggg                                                      20

<210> SEQ ID NO 122
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 122
ggnnnrycgr ynnnnggggg g                                                     21

<210> SEQ ID NO 123
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(16)
<223> OTHER INFORMATION: n is a, c, g, or t

<400> SEQUENCE: 123
ggnnnrycgr ynnnnngggg gg                                              22

<210> SEQ ID NO 124
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 124
ggnnnrycgr ynnnnnnggg ggg                                             23

<210> SEQ ID NO 125
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 125
ggnnnrycgr ynnnnnnngg gggg                                            24

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 126
ggnnnrycgr ynnnnnnnng ggggg                                           25

<210> SEQ ID NO 127
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(20)
<223> OTHER INFORMATION: n is a, c, g, or t

<400> SEQUENCE: 127
ggnnnrycgr ynnnnnnnnn gggggg                                              26

<210> SEQ ID NO 128
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 128
ggnnnrycgr ynnnnnnnnn nggggggg                                            27

<210> SEQ ID NO 129
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 129
ggnnnrycgr ynnnnnnnnn nngggggg                                            28

<210> SEQ ID NO 130
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 130
ggnnnrycgr ynnnnnnnnn nnnggggggg                                          29

<210> SEQ ID NO 131
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

-continued

<221> NAME/KEY: misc_feature
<222> LOCATION: (12)..(24)
<223> OTHER INFORMATION: n is a, c, g, or t

<400> SEQUENCE: 131
ggnnnrycgr ynnnnnnnnn nnnnggggggg                             30

<210> SEQ ID NO 132
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 132
ggnnnrycgr ynnnggggggg g                                       21

<210> SEQ ID NO 133
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 133
ggnnnrycgr ynnnnggggg gg                                       22

<210> SEQ ID NO 134
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 134
ggnnnrycgr ynnnnngggg ggg                                      23

<210> SEQ ID NO 135
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:

```
<221> NAME/KEY: misc_feature
<222> LOCATION: (12)..(17)
<223> OTHER INFORMATION: n is a, c, g, or t

<400> SEQUENCE: 135
ggnnnrycgr ynnnnnnggg gggg                                                24

<210> SEQ ID NO 136
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 136
ggnnnrycgr ynnnnnnngg ggggg                                               25

<210> SEQ ID NO 137
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 137
ggnnnrycgr ynnnnnnnng gggggg                                              26

<210> SEQ ID NO 138
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 138
ggnnnrycgr ynnnnnnnnn ggggggg                                             27

<210> SEQ ID NO 139
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(21)
<223> OTHER INFORMATION: n is a, c, g, or t

<400> SEQUENCE: 139
ggnnnrycgr ynnnnnnnnn nggggggg                                    28

<210> SEQ ID NO 140
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 140
ggnnnrycgr ynnnnnnnnn nnggggggg                                   29

<210> SEQ ID NO 141
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 141
ggnnnrycgr ynnnnnnnnn nnnggggggg                                  30

<210> SEQ ID NO 142
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 142
ggnnnrycgr ynnnnnnnnn nnnnggggggg g                               31

<210> SEQ ID NO 143
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(14)
<223> OTHER INFORMATION: n is a, c, g, or t

<400> SEQUENCE: 143
ggnnnrycgr ynnnggggggg gg                                          22

<210> SEQ ID NO 144
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 144
ggnnnrycgr ynnnnggggg ggg                                          23

<210> SEQ ID NO 145
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 145
ggnnnrycgr ynnnnnggggg gggg                                        24

<210> SEQ ID NO 146
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 146
ggnnnrycgr ynnnnnnggg ggggg                                        25

<210> SEQ ID NO 147
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(18)
<223> OTHER INFORMATION: n is a, c, g, or t

<400> SEQUENCE: 147
ggnnnrycgr ynnnnnnngg gggggg                                    26

<210> SEQ ID NO 148
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 148
ggnnnrycgr ynnnnnnnng ggggggg                                   27

<210> SEQ ID NO 149
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 149
ggnnnrycgr ynnnnnnnnn ggggggg                                   28

<210> SEQ ID NO 150
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 150
ggnnnrycgr ynnnnnnnnn nggggggg                                  29

<210> SEQ ID NO 151
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(22)
<223> OTHER INFORMATION: n is a, c, g, or t

<400> SEQUENCE: 151
ggnnnrycgr ynnnnnnnnn nnggggggggg                              30

<210> SEQ ID NO 152
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 152
ggnnnrycgr ynnnnnnnnn nnnggggggg g                             31

<210> SEQ ID NO 153
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 153
ggnnnrycgr ynnnnnnnnn nnnnggggggg gg                           32

<210> SEQ ID NO 154
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 154
ggnnnrycgr ynnnggggggg ggg                                     23

<210> SEQ ID NO 155
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(15)
<223> OTHER INFORMATION: n is a, c, g, or t

<400> SEQUENCE: 155
ggnnnrycgr ynnnnggggg gggg                                              24

<210> SEQ ID NO 156
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 156
ggnnnrycgr ynnnnngggg ggggg                                             25

<210> SEQ ID NO 157
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 157
ggnnnrycgr ynnnnnnggg gggggg                                            26

<210> SEQ ID NO 158
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 158
ggnnnrycgr ynnnnnnngg ggggggg                                           27

<210> SEQ ID NO 159
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(19)
<223> OTHER INFORMATION: n is a, c, g, or t

<400> SEQUENCE: 159
ggnnnrycgr ynnnnnnnng gggggggg                                              28

<210> SEQ ID NO 160
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 160
ggnnnrycgr ynnnnnnnnn gggggggg                                              29

<210> SEQ ID NO 161
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 161
ggnnnrycgr ynnnnnnnnn nggggggggg                                            30

<210> SEQ ID NO 162
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 162
ggnnnrycgr ynnnnnnnnn nnggggggggg g                                         31

<210> SEQ ID NO 163
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(23)
<223> OTHER INFORMATION: n is a, c, g, or t

<400> SEQUENCE: 163
ggnnnrycgr ynnnnnnnnn nnngggggggg gg                                        32

<210> SEQ ID NO 164
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 164
ggnnnrycgr ynnnnnnnnn nnnngggggg ggg                                        33

<210> SEQ ID NO 165
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 165
ggnnnrycgr ynnngggggg gggg                                                  24

<210> SEQ ID NO 166
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 166
ggnnnrycgr ynnnngggggg ggggg                                                25

<210> SEQ ID NO 167
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

<221> NAME/KEY: misc_feature
<222> LOCATION: (12)..(16)
<223> OTHER INFORMATION: n is a, c, g, or t

<400> SEQUENCE: 167
ggnnnrycgr ynnnnnggggg gggggg    26

<210> SEQ ID NO 168
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 168
ggnnnrycgr ynnnnnnggg ggggggg    27

<210> SEQ ID NO 169
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 169
ggnnnrycgr ynnnnnnngg gggggggg    28

<210> SEQ ID NO 170
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 170
ggnnnrycgr ynnnnnnnng ggggggggg    29

<210> SEQ ID NO 171
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:

```
<221> NAME/KEY: misc_feature
<222> LOCATION: (12)..(20)
<223> OTHER INFORMATION: n is a, c, g, or t

<400> SEQUENCE: 171
ggnnnrycgr ynnnnnnnnn gggggggggg                              30

<210> SEQ ID NO 172
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 172
ggnnnrycgr ynnnnnnnnn ngggggggggg g                           31

<210> SEQ ID NO 173
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 173
ggnnnrycgr ynnnnnnnnn nngggggggg gg                           32

<210> SEQ ID NO 174
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 174
ggnnnrycgr ynnnnnnnnn nnngggggggg ggg                         33

<210> SEQ ID NO 175
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: n is a, c, g, or t
<220> FEATURE:
```

```
<221> NAME/KEY: misc_feature
<222> LOCATION: (12)..(24)
<223> OTHER INFORMATION: n is a, c, g, or t

<400> SEQUENCE: 175
ggnnnrycgr ynnnnnnnnn nnnnggggggg gggg                               34

<210> SEQ ID NO 176
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 176
ggtgcatcga tgcaggggggg                                               20

<210> SEQ ID NO 177
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 177
ggtgcatcga tgcaggggggg                                               20

<210> SEQ ID NO 178
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 178
ggtgcaccgg tgcaggggggg                                               20

<210> SEQ ID NO 179
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 179
atcgactctc gagcgttctc                                                20

<210> SEQ ID NO 180
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 180
tcgtttgttc t                                                         11

<210> SEQ ID NO 181
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 181
tcgagcgttc tc                                                        12
```

METHOD OF TREATING AND PREVENTING INFECTIONS IN IMMUNOCOMPROMISED SUBJECTS WITH IMMUNOSTIMULATORY CPG OLIGONUCLEOTIDES

PRIORITY CLAIM

This claims the benefit of U.S. Provisional Patent Application No. 60/411,944 filed Sep. 18, 2002, which is incorporated by reference herein in its entirety.

FIELD

The present disclosure relates to a method of increasing an immune response to an opportunistic infection in an immunocompromised subject or a subject infected with a lentivirus, specifically to a method of increasing an immune response to a pathogen using oligodeoxynucleotides including a CpG.

BACKGROUND

Primary disorders of the immune system can be divided into four categories, (1) disorders of the humoral immunity, (2) disorders of cellular immunity, (3) disorders of phagocytes, and (4) disorders of complement. In addition, there are many causes of secondary immunodeficiency such as treatment with immunosuppressive or chemotherapeutic agents, protein-losing enteropathy, and infection with a human immunodeficiency virus (HIV). Generally, immunocompromised patients are unable to mount an immune response to a vaccine or an infection in the same manner as non-immunocompromised individuals.

Acquired immunodeficiency syndrome (AIDS) is a disease characterized by a progressive loss of function of the immune system. As a result, those afflicted with the syndrome are susceptible to a variety of opportunistic infections. The etiologic agent of AIDS is a cytopathic retrovirus designated the human immunodeficiency virus (HIV). One of the major targets of the HIV in humans is T helper cells (CD4+ cells). The infection of T helper cells by HIV results in a profound dysregulation of the immune system that includes both depleted numbers and impaired function of T lymphocytes. Although the exact mechanism is unknown, the number of T helper cells predictably declines during HIV infection. Clinicians monitor this decline as an indicator of disease progression.

Opportunistic infections to which individuals infected with HIV are susceptible include bacterial infections such as salmonellosis, syphilis and neurosyphilis, tuberculosis (TB), atypical mycobacterial infection, and bacillary angiomatosis (cat scratch disease), fungal infections such as aspergillosis, candidiasis (thrush, yeast infection), coccidioidomycosis, cryptococcal meningitis, and histoplasmosis, protozoal infections such as cryptosporidiosis, isosporiasis, microsporidiosis, *Pneumocystis Carinii* pneumonia (PCP), and toxoplasmosis, viral infections such as Cytomegalovirus (CMV), hepatitis, herpes simplex (HSV, genital herpes), herpes zoster (HZV, shingles), human papilloma virus (HPV, genital warts, cervical cancer), *Molluscum Contagiosum*, oral hairy leukoplakia (OHL), and progressive multifocal leukoencephalopathy (PML), and neoplasms such as Kaposi's sarcoma, systemic non-Hodgkin's lymphoma (NHL), and primary CNS lymphoma, among others. These opportunistic infections remain principally responsible for the morbidity and mortality associated with HIV disease.

In view of the above, there exists a need for agents that act as immunoprotective agents in immunocompromised individuals.

SUMMARY

Described herein are methods of increasing an immune response to an opportunistic infection in an immunocompromised subject. In one embodiment, the method includes administering to the subject a therapeutically effective amount of an immunostimulatory D oligodeoxynucleotide including a CpG motif, thereby increasing the response to the opportunistic infection. In another embodiment, the method includes administering to the subject a therapeutically effective amount of an immunostimulatory K oligodeoxynucleotide including a CpG motif, thereby increasing the response to the opportunistic infection.

In some embodiments, the subject is infected with a lentivirus, for example, a human immunodeficiency virus or a simian immunodeficiency virus. In some embodiments, the ODN is administered alone, whereas in other embodiments, the ODN is administered in combination with drugs that comprise a highly active anti-retroviral therapy (HAART), for example an anti-retroviral drug such as 3'-azido-3'dexoythymidine (AZT).

In other embodiments, the oligodeoxynucleotide is at least about 16 nucleotides in length and includes a sequence represented by the following formula:

$$5'X_1X_2X_3Pu_1Py_2CpG\ Pu_3Py_3X_4X_5X_6(W)_M(G)_N\text{-}3'\ (SEQ\ ID\ NO: 22)$$

wherein the central CpG motif is unmethylated, Pu is a purine nucleotide, Py is a pyrimidine nucleotide, X and W are any nucleotide, M is any integer from 0 to 10, and N is any integer from 4 to 10. In certain examples, Pu Py CpG Pu Py includes phosphodiester bases, and in certain examples, $X_1X_2X_3$ and $X_4X_5X_6(W)_M(G)_N$ includes phosphodiester bases. In some examples, $X_1X_2X_3$Pu Py and Pu Py $X_4X_5X_6$ are self complementary.

In still other embodiments, the method is a method of increasing an immune response to an opportunistic infection in an immunocompromised subject, including administering to the subject a therapeutically effective amount of an immunostimulatory D oligodeoxynucleotide, thereby increasing the immune response to the opportunistic infection. In yet still other embodiments, the method is a method of increasing an immune response to an opportunistic infection in an immunocompromised subject, including administering to the subject a therapeutically effective amount of an immunostimulatory D oligodeoxynucleotide or an immunostimulatory K oligodeoxynucleotide, wherein an antigenic epitope of a polypeptide is not administered to the subject, thereby increasing the response to the opportunistic infection.

The foregoing and other features and advantages will become more apparent from the following detailed description of several embodiments, which proceeds with reference to the accompanying figures.

BRIEF DESCRIPTION OF THE FIGURES

FIG. 9A is a graph showing the correlation of individual viral loads at the start of the study with the antibody titers developed 45 days after the prime and 45 days after the last immunization. One macaque from the group that received D ODN was euthanized during the study because of intractable diarrhea and weight loss attributed to the SW infection. FIG. 9B is a graph showing the anti-HbsAg antibody levels by animals with viral loads <$10^7$ copies/ml (n=4/group). Animals that received the vaccine alone were unable to mount an antibody response, while those that received K or D ODN together with the HBV vaccine developed significant antibody levels.

SEQUENCE LISTING

Figure 1:
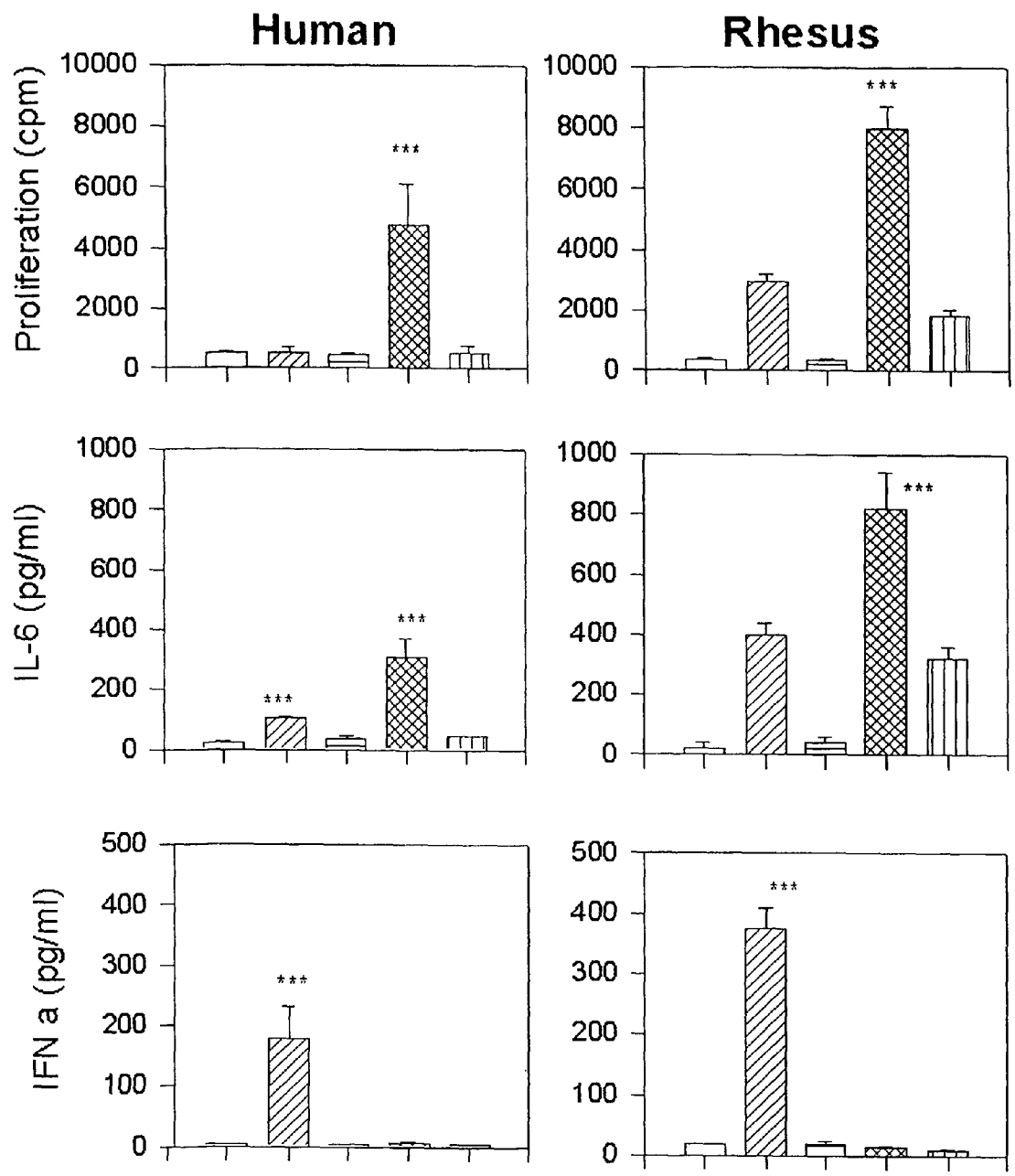
FIG. 1 is a set of graphs showing the response of primate peripheral blood mononuclear cells (PBMC) to K and D oligonucleotides (ODN). PBMC from 8-20 normal human donors and 20 rhesus macaques were stimulated for 72 hours with a panel of K, D or control ODN (3 mM). IL-6 and IFNα levels in culture supernatants were determined by ELISA while cell proliferation was assessed by [H]$^3$ thymidine uptake. Note that D ODN induce the secretion of IFNα while K ODN induce cell proliferation and IL 6 production. The response of PBMC from rhesus macaques mirrors that of human PBMC. All assays were performed in triplicate. Statistical significance was determined by ANOVA of log normalized data. A single asterisk (*) indicates a P value of <0.05; a double asterisk (**) indicates a P value of <0.01.

The nucleic acid sequences listed in the accompanying sequence listing are shown using standard letter abbreviations for nucleotide bases, as defined in 37 C.F.R. 1.822. In the accompanying sequence listing:

SEQ ID NOs: 1-16 are immunostimulatory CpG oligonucleotide sequences.
SEQ ID NOs: 17-18 are SIV primer sequences.
SEQ ID NO: 19 is an SIV-specific probe.
SEQ ID NO: 20 is a K ODN that includes at least about 10 nucleotides described by Formula I.
SEQ ID NO: 21 is a CpG motif in D oligonucleotides described by Formula II.
SEQ ID NO: 22 is an immunostimulatory CpG oligonucleotide sequence.
SEQ ID NOs: 23-98 are immunostimulatory CpG oligonucleotide sequences
SEQ ID NOs: 99-175 are oligodeoxynucleotides that include a sequence represented by Formula IV.
SEQ ID NO: 176 is immunostimulatory CpG oligonucleotide sequence D19.
SEQ ID NO: 177 is immunostimulatory CpG oligonucleotide sequence D35.
SEQ ID NO: 178 is immunostimulatory CpG oligonucleotide sequence D29.
SEQ ID NO: 179 is immunostimulatory CpG oligonucleotide sequence K3.
SEQ ID NO: 180 is immunostimulatory CpG oligonucleotide sequence K123.
SEQ ID NO: 181 is immunostimulatory CpG oligonucleotide sequence K23.

DETAILED DESCRIPTION

I. Abbreviations

A: adenine
Ab: antibody
AIDS: Acquired Immunodeficiency Syndrome
ANOVA: analysis of variance
APC: antigen presenting cell
AVT: 3'-azido-3'dexoy-thymidine
BIV: bovine immunodeficiency virus
BSA: bovine serum albumin
C: cytosine
CAEV: caprine arthritis-encephalitis virus CpG ODN: an oligodeoxynucleotide (either a D or a K type) including a CpG motif
CGD: chronic granulomatous disease
CMV: Cytomegalovirus
CNS: central nervous system
DC: dendritic cell
DNA: deoxyribonucleic acid
EIAV: equine infectious anemia virus
ELISA: Enzyme-Linked Immunosorbent Assay
env: envelope
EU: endotoxin units
FAM: Carboxyfluorescein
FCS: fetal calf serum
FDA: Food and Drug Administration
FIV: feline immunodeficiency virus
G: guanine
h: hour
HAART: highly active anti-retroviral therapy
HbsAg: hepatitis B surface antigen
HBV: hepatitis B virus
HEPES: 4-(2-hydroxyethyl)-1-piperazineethanesulfonic acid
HIV: human immunodeficiency virus
HIV-1: human immunodeficiency virus, type 1
HIV-2: human immunodeficiency virus, type 2
HPV: human papilloma virus
HSV: herpes simplex virus
HZV: herpes zoster virus
i.d. intradermal
IFN-α: interferon alpha
IFN-γ: interferon gamma
µg: microgram
mm: millimeter
mRNA: messenger ribonucleic acid.
NA: nucleoside analog reverse transcriptase inhibitor
NADPH: nicotine amide dinucleotide phosphatase
NHL: non-Hodgkin's lymphoma
NIH: National Institutes of Health
NK: natural killer cells
NNRTI: non-nucleoside analog reverse transcriptase inhibitor
ODN: oligodeoxynucleotide
OHL: oral hairy leukoplakia
ORF: open reading frame
ORN: oligoribonucleotide
PBMC: peripheral blood mononuclear cells
PBS: phosphate buffered saline
PCP: *Pneumocystis Carinii* pneumonia
PCR: polymerase chain reaction
pDC: plasmacytoid dendritic cells
PI: protease inhibitor
PML: progressive multifocal leukoencephalopathy
pol: polymerase
Pu: purine
Py: pyrimidine
RNA: ribonucleic acid
rtPCR: reverse transcriptase polymerase chain reaction
s.c.: subcutaneous
SCID: severe combined immune deficiency
SIV: simian immunodeficiency virus
SIVagm: simian immunodeficiency virus, agm
SIVcol: simian immunodeficiency virus, col
SIVmnd: simian immunodeficiency virus, rmnd
SIVsyk: simian immunodeficiency virus, syk
T: thymine
TB: tuberculosis
TNF: tumor necrosis factor
U: uracil
TAMRA: carboxytetramethyl rhodamine
VL: viral load
VMV: Visna-Maedi virus II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

AIDS: Acquired immunodeficiency syndrome (AIDS) is a disease characterized by a progressive loss of function of the immune system. As a result, those afflicted with the syndrome are susceptible to a variety of opportunistic infections. The etiologic agent of AIDS is a cytopathic retrovirus designated the human immunodeficiency virus (HIV). One of the major targets of the HIV in humans is T helper cells (CD4+ cells). The infection of T helper cells by HIV results in a profound dysregulation of the immune system that includes both depleted numbers and impaired function of T lymphocytes. Although the exact mechanism is unknown, the number of T helper cells predictably declines during HIV infection. Clinicians monitor this decline as an indicator of disease progression.

Animal: Living multi-cellular vertebrate organisms, a category that includes, for example, mammals and birds. The term mammal includes both human and non-human mammals. Similarly, the term "subject" includes both human and veterinary subjects.

Anti-infectious agent: A substance (such as a chemical compound, protein, antisense oligonucleotide, or other molecule) of use in treating infection of a subject. Anti-infectious agents include, but are not limited to, anti-fungals, anti-virals, and antibiotics.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. In one embodiment, an antisense molecule specifically hybridizes to a target mRNA and inhibits transcription of the target mRNA.

CD4: Cluster of differentiation factor 4 polypeptide, a T-cell surface protein that mediates interaction with the MHC class II molecule. CD4 also serves as the primary receptor site for HIV on T-cells during HIV infection.

The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligonucleotides include both D and K oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cytokine: Proteins made by cells that affect the behavior of other cells, such as lymphocytes. In one embodiment, a cytokine is a chemokine, a molecule that affects cellular trafficking.

Epitope: An antigenic determinant. These are particular chemical groups or peptide sequences on a molecule that are antigenic, for example, that elicit a specific immune response. An antibody binds a particular antigenic epitope. Particular HIV epitopes include, but are not limited to Nef, gag-p24, reverse transcriptase, P17 gag.

Functionally Equivalent: Sequence alterations, for example in a D ODN, that yield the same results as described herein. Such sequence alterations can include, but are not limited to, deletions, base modifications, mutations, labeling, and insertions.

Highly active anti-retroviral therapy (HAART): A combination of drugs which, when administered in combination, inhibits a retrovirus from replicating or infecting cells better than any of the drugs individually. In one embodiment, the retrovirus is a human immunodeficiency virus. In one embodiment, the highly active anti-retroviral therapy includes the administration of 3'axido-3-deoxy-thymidine (AZT) in combination with other agents. Examples of agents that can be used in combination in HAART for a human immunodeficiency virus are nucleoside analog reverse transcriptase inhibitor drugs (NA), non-nucleoside analog reverse transcriptase inhibitor drugs (NNRTI), and protease inhibitor drugs (PI). One specific, non-limiting example of HAART used to suppress an HIV infection is a combination of indinavir and efavirenz, an experimental non-nucleoside reverse transcriptase inhibitor (NNRTI).

In one embodiment, HAART is a combination of three drugs used for the treatment of an HIV infection, such as the drugs shown in Table 1 below. Examples of three drug HAART for the treatment of an HIV infection include 1 protease inhibitor from column A plus 2 nucleoside analogs from column B in Table 1. In addition, ritonavir and saquinavir can be used in combination with 1 or 2 nucleoside analogs.

TABLE 1

| Column A | Column B |
| --- | --- |
| indinavir (CRIXIVAN ™) | AZT/ddI |
| nelfinavir (VIRACEPT ™) | d4T/ddI |
| ritonavir (VIRACEPT ™) | AZT/ddC |
| saquinavir (FORTOVASE ™) | AZT/3TC |
| ritonavir/saquinavir | d4T/3TC |

In addition, other 3- and 4-drug combinations can reduce HIV to very low levels for sustained periods. The combination therapies are not limited to the above examples, but include any effective combination of agents for the treatment of HIV disease (including treatment of AIDS).

HIV: (human immunodeficiency virus) is a retrovirus that causes immunosuppression in humans (HIV disease), and leads to a disease complex known as acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T-helper cells.

Immune response: A response of a cell of the immune system, such as a B cell or a T cell to a stimulus. In one embodiment, the response is specific for a particular antigen (an "antigen-specific response").

Immune system deficiency: A disease or disorder in which the subject's immune system is not functioning in normal capacity or in which it would be useful to boost a subject's immune response. In one specific, non-limiting example, a subject with an immune system deficiency has a tumor or cancer (for example, tumors of the brain, lung (for example, small cell and non-small cell), ovary, breast, prostate, colon, or another carcinoma or sarcoma).

Immunocompromised: An immunocompromised subject is a subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer. Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised.

Infectious agent: An agent that can infect a subject, including, but not limited to, viruses, bacteria, and fungi. In one embodiment, an infectious agent is opportunistic.

Examples of infectious viruses include: Retroviridae (for example, human immunodeficiency viruses, such as HIV-1 (also referred to as HTLV-III, LAV or HTLV-III/LAV, or HIV-III) and other isolates, such as HIV-LP; Picornaviridae (for example, polio viruses, hepatitis A virus; enteroviruses, human coxsackie viruses, rhinoviruses, echoviruses); Caliciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, chola Ebola viruses); Paramyxoviridae (for example, parainfluenza viruses, mumps virus, measles virus, respiratory syncytial virus); Orthomyxoviridae (for example, influenza viruses); Bunyaviridae (for example, Hantaan viruses, bunyaviruses, phleboviruses and Nairo viruses); Arenaviridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV)-1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses).

Examples of infectious bacteria include: *Helicobacter pylori, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include, but are not limited to, *Cryptococcus neoformans, Histoplasma capsulatum, Coccidioides immitis, Blastomyces dermatitidis, Chlamydia trachomatis*, and *Candida albicans*.

Other infectious organisms (such as protists) include: *Plasmodium falciparum* and *Toxoplasma gondii*.

Isolated: An "isolated" biological component (such as a nucleic acid, peptide or protein) has been substantially separated, produced apart from, or purified away from other biological components in the cell of the organism in which the component naturally occurs, for example, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

*Lentivirus*: A genus of the family Retroviridae consisting of non-oncogenic retroviruses that produce multi-organ diseases characterized by long incubation periods and persistent infection. Lentiviruses are unique in that they contain open reading frames (ORFs) between the polymerase (pol) and envelope (env) genes and in the 3' env region. Five serogroups are recognized, reflecting the mammalian hosts with which they are associated. Lentiviruses include, but are not limited to human immunodeficiency virus, type 1 (HIV-1), human immunodeficiency virus, type 2 (HIV-2), simian immunodeficiency virus, agm (SIVagm), simian immunodeficiency virus, mnd (SIVmnd), simian immunodeficiency virus, syk (SIVsyk), simian immunodeficiency virus, col (SIVcol), Visna-Maedi virus (VMV), bovine immunodeficiency virus (BIV), feline immunodeficiency virus (Hy), caprine arthritis-encephalitis virus (CAEV), and equine infectious anemia virus (EIAV).

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Maturation: The process in which an immature cell, such as dendritic cell, changes in form or function to become a functional mature cell, such as an APC.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (for example, molecules comprising a sugar (for example, ribose or deoxyribose) linked to a phosphate group and to an exchangeable organic base, which is either a substituted pyrimidine (Py) (for example, cytosine (C), thymine (T) or uracil (U)) or a substituted purine (Pu) (for example, adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (for example, an oligonucleotide minus the phosphate) and any other organic base polymer. Oligonucleotides can be obtained from existing nucleic acid sources (for example, genomic or cDNA), but are preferably synthetic (for example, produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), and phosphodiester and alkylphosphotriesters, in which the charged oxygen moiety is alkylated. Oligonucleotides that contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence and stimulates (for example, has a mitogenic effect) vertebrate immune cells. The cytosine, guanine is unmethylated.

An "oligonucleotide delivery complex" is an oligonucleotide associated with (for example, ionically or covalently bound to; or encapsulated within) a targeting means (for example, a molecule that results in a higher affinity binding to a target cell (for example, a B-cell or natural killer (NK) cell) surface and/or increased cellular uptake by target cells). Examples of oligonucleotide delivery complexes include oligonucleotides associated with: a sterol (for example, cholesterol), a lipid (for example, a cationic lipid, virosome or liposome), or a target cell specific binding agent (for example, a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Opportunistic infection: An infection that occurs in an immunocompromised subject. Opportunistic infections may result from treatments or from alterations in the immune system. The infectious agent can be viral, bacterial, protozoan, or fungal. Opportunistic infections can include, but are not limited to bacterial infections such as salmonellosis, syphilis and neurosyphilis, tuberculosis (TB), atypical mycobacterial infection, and bacillary angiomatosis (cat scratch disease), fungal infections such as aspergillosis, candidiasis (thrush, yeast infection), coccidioidomycosis, cryptococcal meningitis, and histoplasmosis, protozoal infections such as cryptosporidiosis, isosporiasis, microsporidiosis, *Pneumocystis Carinii* pneumonia (PCP), and toxoplasmosis, viral infections such as Cytomegalovirus (CMV), hepatitis, herpes simplex (HSV, genital herpes), herpes zoster (HZV, shingles), human papilloma virus (HPV, genital warts, cervical cancer), *Molluscum Contagiosum*, oral hairy leukoplakia (OHL), and progressive multifocal leukoencephalopathy (PML), and neoplasms such as Kaposi's sarcoma, systemic non-Hodgkin's lymphoma (NHL), and primary CNS lymphoma, among others.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term purified does not require absolute purity; rather, it is intended as a relative term. Thus, for example, a purified nucleotide preparation is one in which the nucleotide is more enriched than the nucleotide is in its natural environment within a cell. Preferably, a preparation is purified such that the nucleotide represents at least 50% of the total peptide or protein content of the preparation.

Retroviruses: RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

Self-complementary nucleic acid sequence: A nucleic acid sequence that can form Watson-Crick base pairs. The four bases characteristic of deoxyribonucleic unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence.

Treatment: Refers to both prophylactic inhibition of initial infection, and therapeutic interventions to alter the natural course of an untreated disease process, such as infection with a virus (for example, HIV infection). "Preventing" a disease refers to inhibiting the full development of a disease, for example in a person who is known to have a predisposition to a disease such a person infected with HIV who does not exhibit the symptoms of AIDS. "Treatment" refers to a therapeutic intervention that ameliorates a sign or symptom of a disease or pathological condition, such as AIDS, after it has begun to develop.

Therapeutically effective dose: A dose sufficient to prevent advancement, or to cause regression of the disease, or which is capable of relieving symptoms caused by the disease, such as pain or swelling.

Vaccine: A preparation of attenuated microorganisms (including but not limited to bacteria and viruses), living microorganisms, antigen, or killed microorganisms, administered for the prevention, amelioration, or treatment of infectious disease.

Virus: A microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

A. D and K-type ODNs

The present disclosure relates to a class of DNA motifs that stimulates immune activation, for example the innate immune response or the adaptive immune response by B cells, monocytes, dendritic cells, and natural killer (NK) cells. K type CpG ODNs have been previously described (see U.S. Pat. Nos. 6,194,388; 6,207,646; 6,214,806; 6,218,371; 6239,116, 6,339,068; 6,406,705, and 6,429,199, which are herein incorporated by reference). K ODNs that exhibit the greatest immunostimulatory activity share specific characteristics. These characteristics differ from those of the Formula II or D ODN (see below). In addition, K ODNs have specific effects on the cells of the immune system, which differ from the effects of D ODN. For example, K ODNs stimulate proliferation of B cells and stimulate the production of IL-6.

The K ODNs include at least about 10 nucleotides and include a sequence represented by Formula I:

5'$N_1N_2N_3$T-CpG-W$N_4N_5N_6$3'          (SEQ ID NO: 20)

wherein the central CpG motif is unmethylated, W is A or T, and $N_1$, $N_2$, $N_3$, $N_4$, $N_5$, and $N_6$ are any nucleotides.

These Formula I or K ODNs stimulate B cell proliferation and the secretion of IgM and IL-6, processes involved in the body's humoral immunity, such as the production of antibodies against foreign antigens. In one embodiment, the K ODNs induce a humoral immune response.

Certain K oligonucleotides are of the formula:

5'$N_1N_2N_3$T-CpG-W$N_4N_5N_6$ 3'          (SEQ ID NO: 20)

and contain a phosphate backbone modification. In one specific, non-limiting example, the phosphate backbone modification is a phosphorothioate backbone modification (for example, one of the non-bridging oxygens is replaced with sulfur, as set forth in International Patent Application WO 95/26204, herein incorporated by reference). In one embodiment, K ODNs have a backbone, and at least one unmethylated CpG dinucleotide. Eliminating the CpG dinucleotide motif from the K ODN significantly reduces immune activation. Incorporating multiple CpGs in a single K ODN increases immune stimulation. In some embodiments, the K ODNs are at least 12 bases long. In addition, K ODNs containing CpG motifs at the 5' end are the most stimulatory, although at least one base upstream of the CpG is required. More particularly, the most active K ODNs contain a thymidine immediately 5' from the CpG dinucleotide, and a TpT or a TpA in a position 3' from the CpG motif. Modifications which are greater than 2 base pairs from the CpG dinucleotide motif appear to have little effect on K ODN activity.

D ODNs differ both in structure and activity from K ODNs. The unique activities of D ODNs are disclosed below (see section C). For example, as disclosed herein, D oligodeoxynucleotides stimulate the release of cytokines from cells of the immune system. In specific, non-limiting examples D oligonucleotides stimulate the release or production of IP-10 and IFN-α by monocytes and/or plasmacytoid dendritic cells and the release or production of IFN-γ by NK cells. The stimulation of NK cells by D oligodeoxynucleotides can be either direct or indirect.

With regard to structure, a CpG motif in D oligonucleotides can be described by Formula II:

5'RY-CpG-RY 3'          (SEQ ID NO: 21)

wherein the central CpG motif is unmethylated, R is A or G (a purine), and Y is C or T (a pyrimidine). D oligonucleotides include an unmethylated CpG dinucleotide. Inversion, replacement, or methylation of the CpG reduces or abrogates the activity of the D oligonucleotide.

Certain D ODNs are at least about 16 nucleotides in length and includes a sequence represented by Formula III:

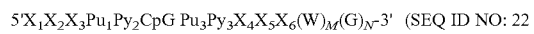
5'$X_1X_2X_3Pu_1Py_2$CpG $Pu_3Py_3X_4X_5X_6(W)_M(G)_N$-3' (SEQ ID NO: 22)

wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1$ $Py_2$ CpG $Pu_3$ $Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN, these nucleotides are termed the 5' far flanking region. Nucleotides 3' of $X_4X_5X_6$ in the D ODN are termed the 3' far flanking region.

In one specific non-limiting example, $Py_2$ is a cytosine. In another specific, non-limiting example, $Pu_3$ is a guanidine. In yet another specific, non-limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific not limiting example, N is from about 4 to about 8. In another specific, non-limiting example, N is about 6.

D CpG oligonucleotides can include modified nucleotides. Without being bound by theory, modified nucleotides can be included to increase the stability of a D oligonucleotide. Without being bound by theory, because phosphorothioate-modified nucleotides confer resistance to exonuclease digestion, the D ODN are "stabilized" by incorporating phosphorothioate-modified nucleotides. In one embodiment, the CpG dinucleotide motif and its immediate flanking regions include phosphodiester rather than phosphorothioate nucleotides. In one specific non-limiting example, the sequence $Pu_1$ $Py_2$ CpG $Pu_3$ $Py_4$ includes phosphodiester bases. In another specific, non-limiting example, all of the bases in the sequence $Pu_1$ $Py_2$ CpG $Pu_3$ $Py_4$ are phosphodiester bases. In yet another specific, non-limiting example, $X_1X_2X_3$ and $X_4X_5X_6(W)_m (G)_N$ include phosphodiester bases. In yet another specific, non-limiting example, $X_1X_2X_3$ $Pu_1$ $Py_2$ CpG $Pu_3$ $Py_4$ $X_4X_5X_6$ $(W)_M (G)_N$ include phosphodiester bases. In further non-limiting examples the sequence $X_1X_2X_3$ includes at most one or at most two phosphorothioate bases and/or the sequence $X_4X_5X_6$ includes at most one or at most two phosphorothioate bases. In additional non-limiting examples, $X_4X_5X_6$ (W)M (G)N includes at least 1, at least 2, at least 3, at least 4, or at least 5 phosphorothioate bases. Thus, a D oligodeoxynucleotide can be a phosphorothioate/phosphodiester chimera.

As disclosed herein, any suitable modification can be used in the present disclosure to render the D oligodeoxynucleotide resistant to degradation in vivo (for example, via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (for example, the charged phosphonate oxygen is replaced with an alkyl or aryl group, as set forth in U.S. Pat. No. 4,469,863), phosphodiesters and alkylphosphotriesters (for example, the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D oligodeoxynucleotides can also be modified to contain a secondary structure (for example, stem loop structure). Without being bound by theory, it is believed that incorporation of a stem loop structure renders and oligodeoxynucleotide more effective.

In a further embodiment, $Pu_1 Py_2$ and $Pu_3 Py_4$ are self-complementary. In another embodiment, $X_1X_2X_3$ and $X_4X_5X_6$ are self complementary. In yet another embodiment $X_1X_2X_3 Pu_1 Py_2$ and $PU_3 Py_4 X_4X_5X_6$ are self complementary.

Specific non-limiting examples of a D oligonucleotide wherein $Pu_1 Py_2$ and $Pu_3 Py_4$ are self-complementary include, but are not limited to, ATCGAT (SEQ ID NO: 9), ACCGGT (SEQ ID NO: 10), ATCGAC (SEQ ID NO: 11), ACCGAT (SEQ ID NO: 12), GTCGAC (SEQ ID NO: 13), or GCCGGC (SEQ ID NO: 14). Without being bound by theory, the self-complementary base sequences can help to form a stem-loop structure with the CpG dinucleotide at the apex to facilitate immunostimulatory functions. Thus, in one specific, non-limiting example, D oligonucleotides wherein $Pu_1 Py_2$ and $Pu_3 Py_4$ are self-complementary induce higher levels of IFN-γ production from a cell of the immune system (see below). The self-complementary need not be limited to $Pu_1 Py_2$ and $Pu_3 Py_4$. Thus, in another embodiment, additional bases on each side of the three bases on each side of the CpG-containing hexamer form a self-complementary sequence (see above).

One specific, non-limiting example of a sequence wherein $Pu_1 Py_2$ and $Pu_3 Py_4$ are self-complementary, but wherein the far-flanking sequences are not self-complementary is:

GGTGCATCGATACAGGGGGG (ODN D 113, SEQ ID NO:15).

This oligodeoxynucleotide has a far flanking region that is not self complementary and induces high levels of IFN-γ and IFN-α.

Another specific, non-limiting example of a D oligodeoxynucleotides is:

GGTGCGTCGATGCAGGGGGG (D28, SEQ ID NO: 16).

This oligodeoxynucleotide is of use for inducing production and/or release of cytokines from immune cells, although it lacks a self-complementary motif.

In one embodiment, the D oligodeoxynucleotides disclosed herein are at least about 16 nucleotides in length. In a second embodiment, a D oligodeoxynucleotide is at least about 18 nucleotides in length. In another embodiment, a D oligodeoxynucleotide is from about 16 nucleotides in length to about 100 nucleotides in length. In yet another embodiment, a D oligodeoxynucleotide is from about 16 nucleotides in length to about 50 nucleotides in length. In a further embodiment, a D oligodeoxynucleotide is from about 18 nucleotides in length to about 30 nucleotides in length.

In another embodiment, the oligodeoxynucleotide is at least 18 nucleotides in length, and at least two Gs are included at the 5' end of the molecule, such that the oligodeoxynucleotide includes a sequence represented by Formula IV:

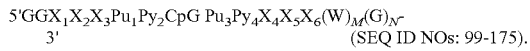

5'GGX$_1$X$_2$X$_3$Pu$_1$Py$_2$CpG Pu$_3$Py$_4$X$_4$X$_5$X$_6$(W)$_M$(G)$_N$-3' (SEQ ID NOs: 99-175).

The D oligodeoxynucleotide can include additional Gs at the 5' end of the oligodeoxynucleotide. In one specific example, about 1 or about 2 Gs are included at the 5' end of an oligodeoxynucleotide including a sequence as set forth as Formula IV.

Examples of a D oligodeoxynucleotide include, but are not limited to:

```
5'XXTGCATCGATGCAGGGGGG3'     (SEQ ID NO: 1)
5'XXTGCACCGGTGCAGGGGGG3',    (SEQ ID NO: 2)
5'XXTGCGTCGACGCAGGGGGG3',    (SEQ ID NO: 3)
5'XXTGCGTCGATGCAGGGGGG3',    (SEQ ID NO: 4)
5'XXTGCGCCGGCGCAGGGGGG3',    (SEQ ID NO: 5)
5'XXTGCGCCGATGCAGGGGGG3',    (SEQ TD NO: 6)
5'XXTGCATCGACGCAGGGGGG3',    (SEQ ID NO: 7)
5'XXTGCGTCGGTGCAGGGGGG3',    (SEQ ID NO: 8)
``` wherein X any base, or is no base at all. In one specific, non-limiting example, X is a G. In particular, non-limiting examples, the oligodeoxynucleotide includes a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

The oligodeoxynucleotides disclosed herein can be synthesized de novo using any of a number of procedures well known in the art. For example, the oligodeoxynucleotides can be synthesized as set forth in U.S. Pat. No. 6,194,388, which is herein incorporated by reference in its entirety. A D oligodeoxynucleotide may be synthesized using, for example, the B-cyanoethyl phosphoramidite method or nucleoside H-phosphonate method. These chemistries can be performed by a variety of automated oligonucleotide synthesizers available in the market. Alternatively, oligodeoxynucleotides can be prepared from existing nucleic acid sequences (for example, genomic or cDNA) using known techniques, such as employing restriction enzymes, exonucleases or endonucleases, although this method is less efficient than direct synthesis.

B. Pharmaceutical Compositions

The immunostimulatory ODNs described herein may be formulated in a variety of ways depending on the type of disease to be treated. Pharmaceutical compositions are thus provided for both local use as well as for systemic use. Therefore, the disclosure includes within its scope pharmaceutical compositions comprising at least one immunostimulatory ODN formulated for use in human or veterinary medicine.

Pharmaceutical compositions that include at least one immunostimulatory ODN as described herein as an active ingredient, or that include both an immunostimulatory ODN and an additional anti-viral, immunomodulatory, or anti-infective agent as active ingredients, may be formulated with an appropriate solid or liquid carrier, depending upon the particular mode of administration chosen. Additional active ingredients include, for example, antivirals such as AL-721

(from Ethigen of Los Angeles, Calif.), recombinant human interferon beta (from Triton Biosciences of Alameda, Calif.), Acemannan (from Carrington Labs of Irving, Tex.), ganciclovir (from Syntex of Palo Alto, Calif.), didehydrodeoxythymidine or d4T (from Bristol-Myers-Squibb), EL10 (from Elan Corp, of Gainesville, Ga.), dideoxycytidine or ddC (from Hoffman-LaRoche), Novapren (from Novaferon Labs, Inc, of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others, immuno-modulators such as AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG™ (from Imreg of New Orleans, La.), SK&F106528, TNF (Genentech), and soluble TNF receptors (Immunex), anti-infectives such as clindamycin with primaquine (from Upjohn, for the treatment of *pneumocystis* pneumonia), fluconazlone (from Pfizer for the treatment of cryptococcal meningitis or candidiasis), nystatin, pentamidine, trimethaprim-sulfamethoxazole, and many others, and agents used in HAART therapy, such as nucleoside analog reverse transcriptase inhibitor drugs (NA), non-nucleoside analog reverse transcriptase inhibitor drugs (NNRTI), protease inhibitor drugs (PI).

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutical compositions that comprise an immunostimulatory ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

C. Therapeutic Uses

A method is disclosed herein for increasing an immune response to an opportunistic infection in an immunocompromised subject. Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer. Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised. The subject can be a human or a non-human mammal, such as a primate.

In some embodiments, the immunocompromised subject is infected with a lentivirus. Lentiviruses include, but are not limited to human immunodeficiency virus type 1 (HIV-1), human immunodeficiency virus type 2 (HIV-2), simian immunodeficiency virus agm (SIVagm), simian immunodeficiency virus mnd (SIVmnd), simian immunodeficiency virus syk (SIVsyk), simian immunodeficiency virus col (SIVcol), Visna-Maedi virus (VMV), bovine immunodeficiency virus (BIV), feline immunodeficiency virus (FIV), caprine arthritis-encephalitis virus (CAEV), and equine infectious anemia virus (EIAV). In some embodiments, the lentivirus is human immunodeficiency virus type 1 (HIV-1). In some embodiments, the lentivirus is human immunodeficiency virus type 2 (HIV-2).

In some embodiments, the opportunistic infection is infection with *Leishmania major*. In other embodiments, the opportunistic infection is a bacterial infection such as salmonellosis, syphilis and neurosyphilis, tuberculosis (TB), atypical mycobacterial infection, and bacillary angiomatosis (cat scratch disease), a fungal infection such as aspergillosis, candidiasis (thrush, yeast infection), coccidioidomycosis, cryptococcal meningitis, and histoplasmosis, protozoal infections such as cryptosporidiosis, isosporiasis, microsporidiosis, *Pneumocystis Carinii* pneumonia (PCP), and toxoplasmosis, or a viral infection such as Cytomegalovirus (CMV), hepatitis, herpes simplex (HSV, genital herpes), herpes zoster (HZV, shingles), human papilloma virus (HPV, genital warts, cervical cancer), *Molluscum Contagiosum*, oral hairy leukoplakia (OHL), and progressive multifocal leukoencephalopathy (PML), and neoplasms, such as Kaposi's sarcoma, systemic non-Hodgkin's lymphoma (NHL), and primary CNS lymphoma, among others.

In order to increase an immune response to an opportunistic infection in a subject infected with a lentivirus, a therapeutically effective amount of a D or K ODN (see above) is administered to the subject. In some embodiments, the oligodeoxynucleotide is a D oligodeoxynucleotide, and in some examples, the oligodeoxynucleotide is at least about 16 nucleotides in length and comprises a sequence represented by the following formula:

5'$X_1X_2X_3Pu_1Py_2CpG\ Pu_3Py_4X_4X_5X_6(W)_M(G)_N$-3' (SEQ ID NO: 22)

wherein the central CpG motif is unmethylated, Pu is a purine nucleotide, Py is a pyrimidine nucleotide, X and W are any nucleotide, M is any integer from 0 to 10, and N is any integer from 4 to 10. In particular examples of certain embodiments, N is about 6. In other examples, Pu Py CpG Pu Py includes phosphodiester bases, and in particular examples, $Pu_1\ Py_2\ CpG\ Pu_3\ Py_4$ are phosphodiester bases.

In some embodiments, $X_1X_2X_3$ and $X_4X_5X_6(W)_M\ (G)_N$ includes phosphodiester bases. In particular examples, $X_1X_2X_3$ includes one or more phosphorothioate bases, and in other examples, $X_4X_5X_6(W)_M (G)_N$ includes one or more phosphorothioate bases. In still other embodiments $X_1X_2X_3$ Pu Py and Pu Py $X_4X_5X_6$ are self complementary, and in further embodiments, the lentiviral infection is treated in a subject without stimulating expression of CD4 in T cells of the subject.

In some embodiments, the method includes administering to the subject a therapeutically effective amount of an immunostimulatory D oligodeoxynucleotide or an immunostimulatory K oligodeoxynucleotide, and an antigenic epitope of a polypeptide is not administered to the subject.

The method includes administering a therapeutically effective amount of a D oligodeoxynucleotide or a K oligodeoxynucleotide to a subject infected with a lentivirus, thereby treating the subject. In one embodiment, the ODN can be administered locally, such as by topical application or intradermal administration. For intradermal injection, for example, ODN are injected into the skin at the site of interest. ODNs can be injected, for example, once, or they may be injected in divided doses two or more times, for example monthly, weekly, daily, or 2-4 times daily. In other embodiments, the administration of the ODN is systemic. Oral, intravenous, intra-arterial, subcutaneous, intra-peritoneal, intramuscular, inhalational, and even rectal administration is contemplated.

In some embodiments the method includes administering to the subject a therapeutically effective amount of an immunostimulatory D oligodeoxynucleotide or an immunostimulatory K oligodeoxynucleotide, and an antigenic epitope of a polypeptide is not administered to the subject. The method results in an increased response to an opportunistic infection.

D. Combination Therapy

The present methods also include combinations of the ODNs disclosed herein with one or more drugs useful in the treatment of an opportunistic infection. For example, the ODNs disclosed herein may be administered, whether before or after exposure to a virus, in combination with effective doses of other anti-virals, immunomodulators, anti-infectives, or vaccines. The term "administration" refers to both concurrent and sequential administration of the active agents.

In one embodiment, a combination of ODN with one or more agents useful in the treatment of a lentiviral disease is provided. In one specific, non-limiting example, the lentiviral disease is an HIV-1-induced, an HIV-2-induced, a SIV-induced, or a FIV induced disease.

Specific, non-limiting examples of antivirals include: AL-721 (from Ethigen of Los Angeles, Calif.), recombinant human interferon beta (from Triton Biosciences of Alameda, Calif.), Acemannan (from Carrington Labs of Irving, Tex.), ganciclovir (from Syntex of Palo Alto, Calif.), didehydrodeoxythymidine or d4T (from Bristol-Myers-Squibb), EL10 (from Elan Corp, of Gainesville, Ga.), dideoxycytidine or ddC (from Hoffman-LaRoche), Novapren (from Novaferon Labs, Inc, of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Specific, non-limiting examples of immuno-modulators are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG™ (from Imreg of New Orleans, La.), SK&F106528, TNF (Genentech), and soluble TNF receptors (Immunex).

Specific, non-limiting examples of some anti-infectives used include clindamycin with primaquine (from Upjohn, for the treatment of pneumocystis pneumonia), fluconazlone (from Pfizer for the treatment of cryptococcal meningitis or candidiasis), nystatin, pentamidine, trimethaprim-sulfamethoxazole, and many others.

"Highly active anti-retroviral therapy" or "HAART" refers to a combination of drugs that, when administered in combination, inhibits a retrovirus from replicating or infecting cells better than any of the drugs individually. In one embodiment, the retrovirus is a human immunodeficiency virus. In one embodiment, the highly active anti-retroviral therapy includes the administration of 3'axido-3-deoxy-thymidine (AZT) in combination with other agents, such as a D ODN. Specific, non-limiting examples of agents that can be used in combination in HAART for a human immunodeficiency virus are nucleoside analog reverse transcriptase inhibitor drugs (NA), non-nucleoside analog reverse transcriptase inhibitor drugs (NNRTI), and protease inhibitor drugs (PI). One specific, non-limiting example of HAART used to suppress an HIV infection is a combination of indinavir and efavirenz, an experimental non-nucleoside reverse transcriptase inhibitor (NNRTI).

In one embodiment, HAART is a combination of three drugs used for the treatment of an HIV infection, such as the drugs shown in Table 2 below. Examples of three drug HAART for the treatment of an HIV infection include 1 protease inhibitor from column A plus 2 nucleoside analogs from column B in Table 2. In addition, ritonavir and saquinavir can be used in combination with 1 or 2 nucleoside analogs.

TABLE 2

| Column A | Column B |
| --- | --- |
| indinavir (CRIXIVAN ™) | AZT/ddI |
| nelfinavir (VIRACEPT ™) | d4T/ddI |
| ritonavir (NORVIR ™) | AZT/ddC |
| saquinavir (FORTOVASE ™) | AZT/3TC |
| ritonavir/saquinavir | d4T/3TC |

In addition, other 3- and 4-drug combinations can reduce HIV to very low levels for sustained periods. The combination therapies are not limited to the above examples, but include any effective combination of agents for the treatment of HIV disease (including treatment of AIDS).

The disclosure is illustrated by the following non-limiting Examples.

EXAMPLES

Example 1

General Methods

Human PBMC:

Buffy coats from healthy blood donors were obtained from the NIH Department of Transfusion Medicine. PBMC from HIV infected subjects were obtained from the Infectious Diseases Section of the Department of Transfusion Medicine at the National Institutes of Health Blood Bank and from the National Institute of Allergy and Infectious Diseases, NIH.

Rhesus Monkeys:

Healthy 3 year old rhesus macaques (M. mulata) were obtained from the FDA colony in South Carolina. Animals were monitored daily by veterinarians. No systemic or local adverse reactions to CpG ODN were observed. Treatments were administered and peripheral blood samples obtained from ketamine anesthetized animals (10 mg/kg, Ketaject, Phoenix Pharmaceuticals, St Joseph, Md.).

Mononuclear Cell Preparation:

Human and monkey mononuclear cells were isolated by density gradient centrifugation of PBMC over Ficoll Hypaque density gradient medium FICOLL™-Hypaque as described. Cells were washed three times and cultured in RPMI 1640 supplemented with 10% heat-inactivated fetal calf serum (FCS), 1.5 mM L-glutamine and 100 U/ml of penicillin/streptomycin at $5 \times 10^5$ cells/well in the presence of 1-3 µM ODN. Supernatants were collected after 72 hours and tested by ELISA for cytokine and antibody levels.

Treatment Groups and Protocol:

For the first study 18 healthy rhesus macaques were challenged on the forehead on day 0 with $10^8$ L. amazonensis (PH8) metacyclic promastigotes intradermally (i.d.) as previously described (R. Kenney et al., 1999, J. I. 163:4481-4488; Verthelyi et al., 2002, J. I. 168:1659-1663). Three days before and three days after the infectious challenge, monkeys (six per group) were treated i.d. at the site of the challenge with 500 µg of a mix of K or D ODN previously shown to stimulate rhesus macaques (Verthelyi et al., 2002, J. I. 168: 1659-1663). Control monkeys (n=6) received saline. The monkeys developed a typical self-limited lesion in situ characterized by erythema, induration, and ulceration. Lesion size, which reflects the severity of infection, was calculated from the average diameter to approximate a circle, measuring length by width was measured weekly in a blinded fashion. For the second study, 14 monkeys that had been infected with SIV (SIVmac 239/CEMx174 CL#215; 100 MID$_{50}$ intrarectally) one year before were challenged with $10^7$ L. major metacyclic promastigotes (WHOM/IR/-/173). Three days before and three days after the challenge they were treated id. with D (n=4), K (n=4) or control (n=3) ODN at the site of challenge. Monkeys that received saline served as untreated controls. The size of the lesions and the viremia that developed was measured weekly. On day 56, the lesions were biopsied, the animals euthanized and the local and systemic parasitic load measured.

Experimental Infections:

L. amazonensis (PH8) was obtained from American Type Culture Collection (Manassas, Va.) and grown for infection. Promastigotes were grown in medium 199 with 20% FCS, supplemented by 0.1 mM adenine (Life Technologies, Gaithersburg, Md.), 25 mM HEPES (Life Technologies), 5 g/ml hemin (Sigma, St. Louis, Mo.), 1 µg/ml biotin (Life Technologies), and Pen/Strep/L-glutamine (Life Technologies). To ensure high infectivity, the strain was passed through BALB/c mice once and frozen as amastigotes for storage. These amastigotes were freshly transformed in culture to promastigotes, then grown to late log phase for each experiment. After washing the cells, metacyclic promastigotes were purified by negative selection using mAb D5, which recognizes a surface lipophosphoglycan determinant that is differentially expressed by procyclic and other immature stages of L. amazonensis promastigotes. The promastigotes were incubated for 30 minutes at room temperature with a 1/200 dilution of D5 ascites, and the agglutinated parasites were pelleted by low-speed centrifugation at 400×g for five minutes. Metacyclic promastigotes remaining in suspension were pelleted and washed, then resuspended at $1 \times 10^8$ promastigotes/ml in RPMI. Monkeys were challenged by injection with $1 \times 10^7$ metacyclic promastigotes in 0.1 ml in the forehead.

L. major clone V1 (MHOM/IL/80/Friedlin) promastigotes were grown at 26° C. in medium 199 supplemented as described above. Infective-stage metacyclic promastigotes were isolated from 4-5 day old stationary cultures by negative selection using peanut agglutinin (Vector Laboratories, Burlingame, Calif.).

Oligodeoxynucleotides:

ODN were synthesized by the CBER Core Facility. All ODN had less than <0.1 EU of endotoxin per mg of ODN as assessed by a Limulus amebocyte lysate assay (QCL-1000, BioWhittaker). Individual humans and monkeys vary in their response to specific K and D ODNs. Indeed, no single D or K CpG motif is optimally stimulatory in all donors. However, mixtures of ODNs were identified that strongly stimulated PBMC from all human donors. These D or K ODN mixtures were used in the in vivo studies in macaques (Verthelyi et al., 2002, J. Immunology 168:1659-1663).

Antibodies:

Cross-reactive Abs that recognized human and macaque IL-6 (R&D, Minneapolis, Minn.) and IFNγ(PBL Biomedical Laboratories, New Brunswick, N.J.) were used in ELISA assays.

ELISA:

Microtiter plates (96-well, Millipore Corp., Bedford, Mass.) were coated with anti-cytokine Ab and blocked with PBS-5% BSA (Verthelyi et al., J. Immunology, 2001, 166: 2372). Culture supernatants from PBMC cultures were added, and their cytokine content quantitated by the additional of biotin-labeled anti-cytokine Ab followed by phosphatase-conjugated avidin and phosphatase-specific colorimetric substrate. Standard curves were generated using known amounts of recombinant human cytokine. All assays were performed in triplicate. When supernatants from HIV/SIV-infected PBMC were used, Triton X100 was used to inactivate the virus.

Flow Cytometry:

Cells cultured for various periods with D ODN were washed in cold PBS, fixed and stained with fluorescent labeled antibodies to CD83, CD86, CD14, MHC class II. Samples were washed and analyzed (20,000-40,000 events) on a FACScan flow cytometer (Becton Dickinson, San Jose, Calif.) after gating on monocytes with proper electronic compensation. The data were analyzed with CeliQUest software Becton Dickinson).

Cell Proliferation Assay:

$10^5$ PBMC/well were incubated with 3 µM of ODN for 68 hours, pulsed with 1 µCi of [$^3$H] thymidine and harvested four hours later. All assays were performed in triplicate. Intraassay variation was <15%.

Viral Load Measurements:

Particle-associated SIV RNA in plasma was quantitated using a modification of a previously described real-time reverse transcription-PCR (RT-PCR) assay for SIV gag RNA, on a Prism 7700 sequence detection system (PE Biosystems, Foster City, Calif.). Specimen preparation and reverse transcription with random priming were as previously described (Silverstein et al., J. Virol. 2000 November; 74(22): 10489-10497). For PCR amplification of the resulting cDNA, the following primers and biterminally labeled and 3'-blocked probe were used: forward primer (SGAG21), 5'-gTC TgC gTC ATP Tgg TgC ATT C-3' (SEQ ID NO: 17); reverse primer (SGAG22), 5'-CAC TAg KTg TCT CTg CAC TAT PTg TTT Tg-3'(SEQ ID NO: 18); and probe (P-SGAG23), 5'-(FAM)CTT CPT CAg TKT gTT TCA CTT TCT CTT CTg Cg(TAMRA) 3' (SEQ ID NO: 19), where P and K are modified bases (Glen Research catalog no. 10-1047-90 and 10-1048-90, respectively), introduced to minimize the impact of potential sequence mismatches at positions of described heterogeneity among SIV isolates (Los Alamos HIV sequence database, available on the internet), and FAM and TAMRA indicate the reporter fluorochrome 6-carboxy-fluorescein and the quencher fluorochrome 6-carboxy-tetramethylrhodamine, respectively. After ten minutes at 95° C. to activate the Taq Gold polymerase, 45 cycles of amplification were performed (consisting of 95° C. for 15 and 60° C. for 60 seconds), and the nominal SIV gag copy number for test specimens was determined by interpolation of the average measured threshold cycle number for duplicate determinations onto a standard curve of threshold cycle number versus known input template copy number for a purified in vitro transcript control template, essentially as described previously (Silverstein et al., *J. Virol.* 2000 November; 74(22): 10489-10497).

The threshold sensitivity of the assay is 100 copy Eq/ml of plasma, with an average inter-assay coefficient of variation of <25%.

Statistical Analysis:

Statistically significant differences in cytokine and cell proliferation levels were determined using a 2-tailed nonparametric Rank Sum test or ANOVA with Dunnett's post test analysis. Differences in lesion sizes were tested by Friedman Repeated-Measures Analysis on Ranks with Tukey's All Pairwise Multiple Comparison Procedure using Sigma Stat.

Example 2

Immunoprotective Activity of CpG ODN In Vivo

Figure 2:
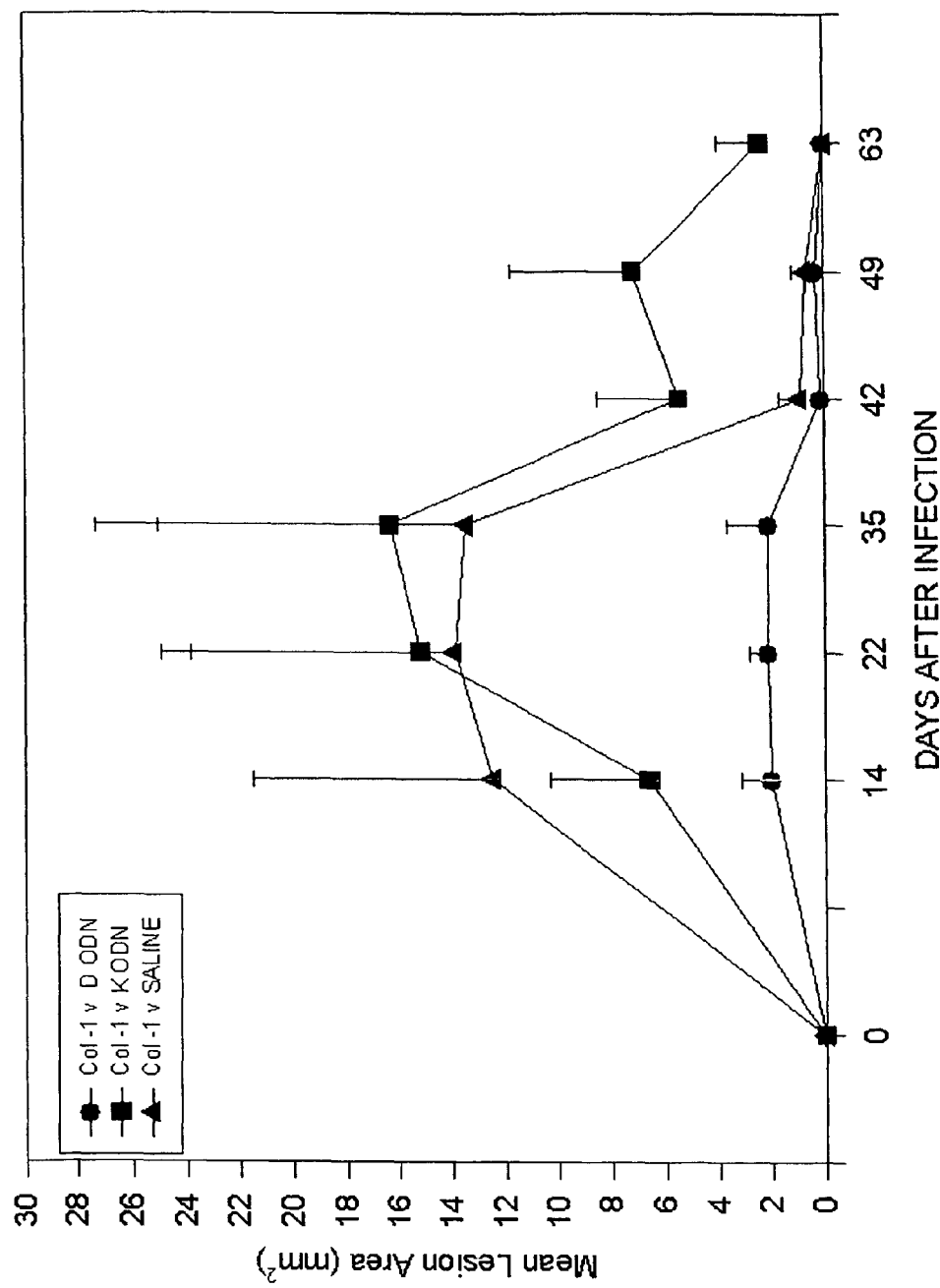
FIG. 2 is a graph showing that treatment of primates with CpG D ODN protects them from a local challenge with pathogenic *Leishmania* parasites. Treatment of the macaques with D ODN, but not with K ODN, significantly reduced the size of the cutaneous lesion ($p<0.001$).

Previous studies had established that treatment with CpG ODN protected mice from up to $10^4$ L metacyclic parasites). In order to determine whether CpG ODNs were able to exert a similar protective effect in primates we utilized a non-human primate model for leishmaniasis. Eighteen rhesus macaques were treated with 500 μg of either D or K CpG ODN mixes previously shown to be active on PBMC of non-human primates (Verthelyi et al., 2002, *J. I.* 168:1659-1663). In situ intradermal (i.d.) inoculation was carried out three days before and three days after challenge with *L. amazonensis* in the skin of the forehead. As previously described, intradermal inoculation with $10^8$ *L. amazonensis* induced the development of a cutaneous *Leishmania* lesion that resembles the ones observed in humans. In untreated monkeys its peak surface area was of 14±10 mm² on day 22. As shown in FIG. 2, treatment of the macaques with D ODN, but not with K ODN, significantly reduced the size of the cutaneous lesion (p<0.001). This shows that treatment of primates with CpG D ODN protect them from a local challenge with pathogenic *Leishmania* parasites.

Example 3

PBMC From HIV Infected Subjects Respond to CpG ODN

HIV infection is associated with a progressive loss of immune function and increased susceptibility to opportunistic infections such as *L. major*. In addition to the gradual loss of CD4+ T cells, there is a reduction in number and function of plasmacytoid dendritic cells (pDC) and natural killer (NK) cells leading to impaired immune responses and increase susceptibility to opportunistic infections (Chehimi, 2002, *J. I.*:168: 4796-4801; Azzoni et al., 2002 *J. I.* 168:5764-5770). In order to assess whether PBMC from HIV infected patients would be responsive to CpG ODN activation, the response of PBMC from 43 HIV-infected (Table 3) and 16 healthy individuals to D and K CpG ODN was compared in vitro.

Figure 3:
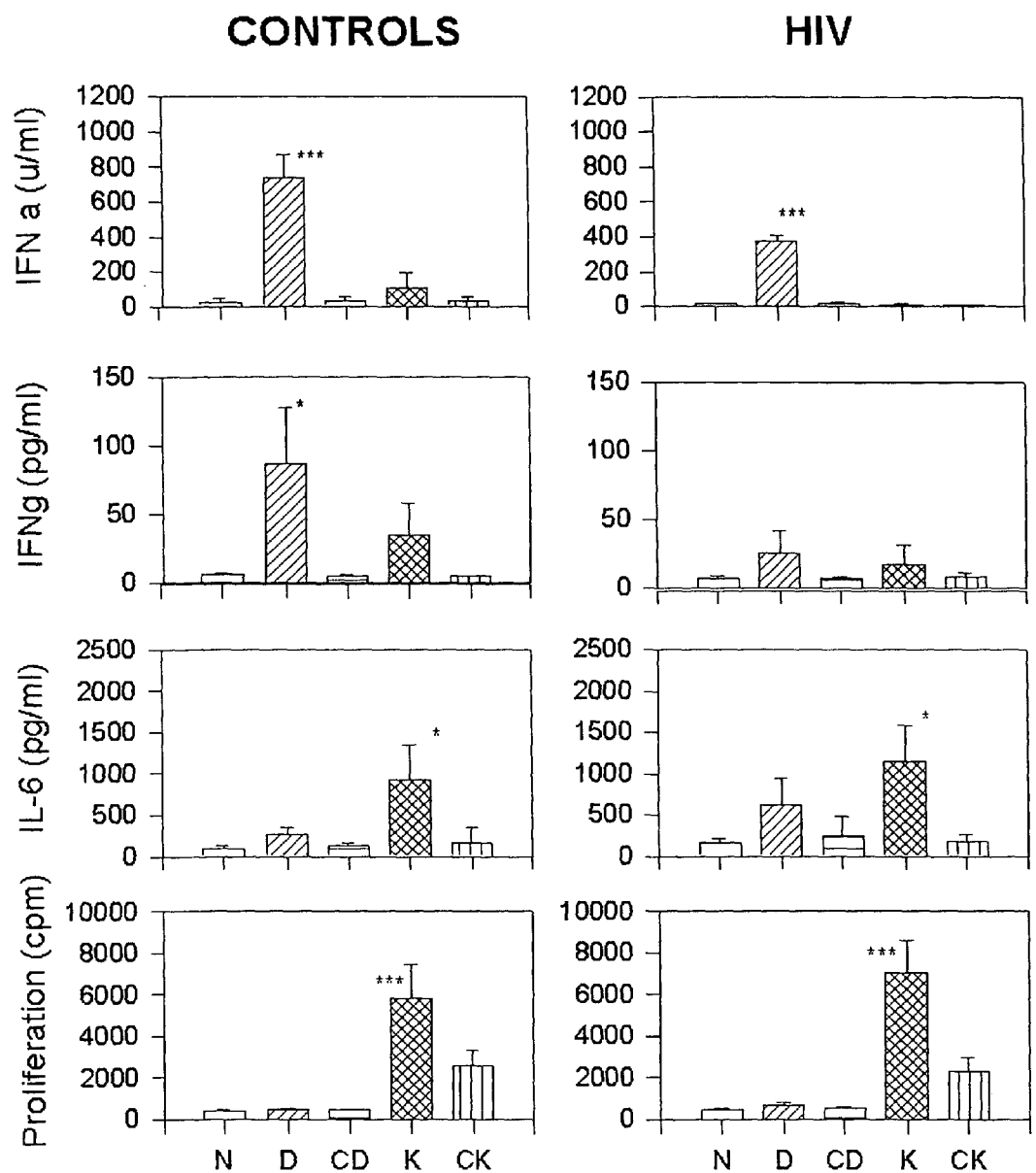
FIG. 3 is a set of graphs showing that D ODNs trigger the secretion of IFNα and IFNγ. In contrast, K ODNs increase cell proliferation and IL-6 production. PBMC from healthy and HIV infected subjects secreted similar levels of IFNα and IFNγ in the absence of stimulation or in the presence of control ODN lacking the CpG motif. Upon stimulation with CpG D ODN, however, PBMC from HIV infected subjects generated significantly lower IFNγ($p<0.05$) or IFNα than healthy controls ($p<0.001$).
Figure 4:
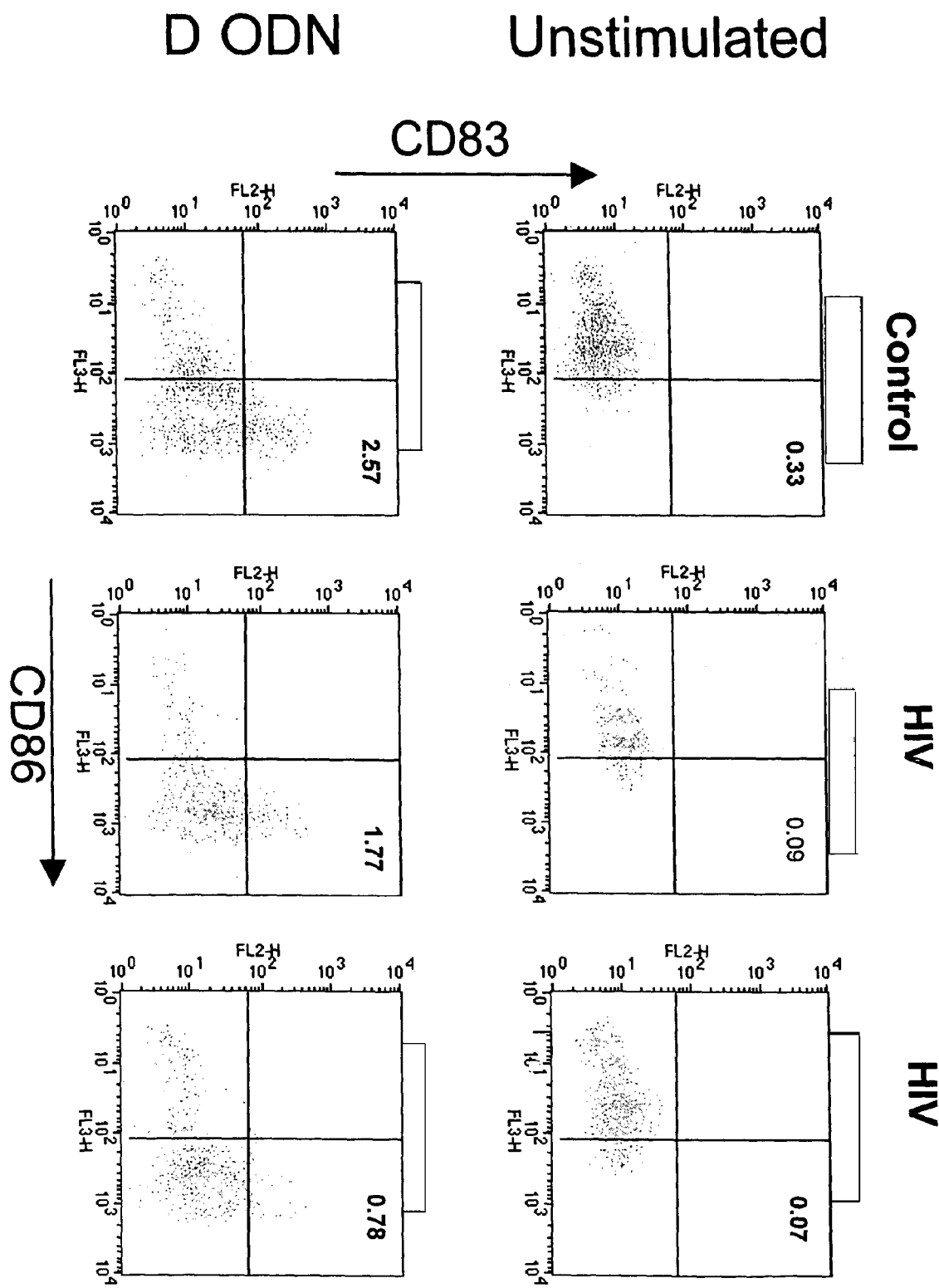
FIG. 4 is a graph showing that D ODNs induce dendritic cell (DC) maturation.
Figure 5:
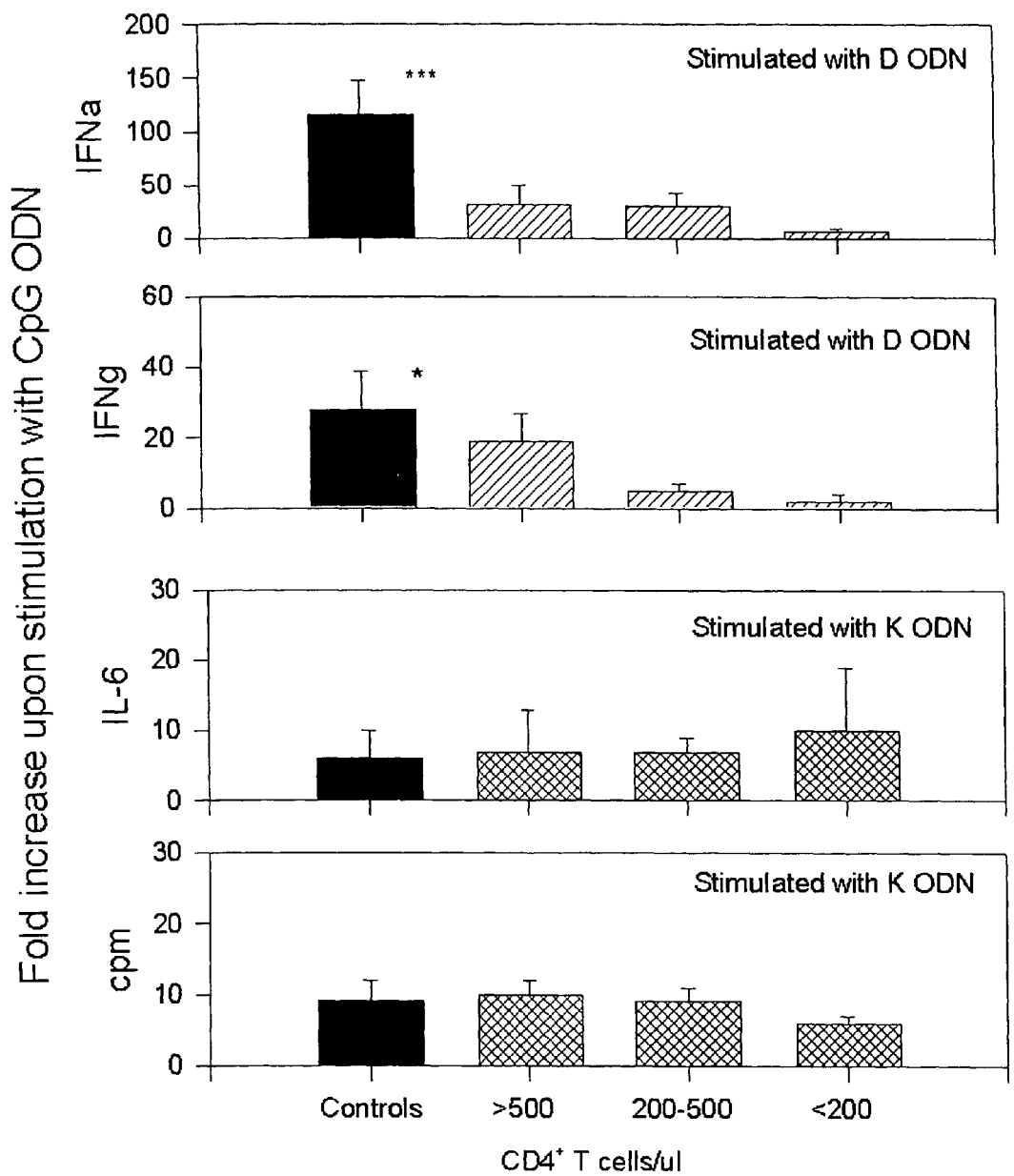
FIG. 5 is a set of graphs demonstrating that the response to K ODNs is not significantly different in PBMC from HIV infected and healthy subjects, indicating that B cells and monocytes retain their ability to respond to CpG ODN. These data show that PBMC from HIV infected subjects are activated by CpG ODN in vitro. The responsiveness to CpG ODN, although reduced, is evident even among patients with high viral loads and low CD4+ T cells. The reduction in IFNα and IFNγ secretion correlated directly with the number of CD4+ T cells ($p<0.01$).

As previously shown, the response elicited by PBMC from healthy subjects to the two types of CpG ODN was distinct: D ODN triggered the secretion of IFNα and IFNγ (FIG. 3), and induced DC maturation (FIG. 4). In contrast, K ODN increased cell proliferation and IL-6 production (FIG. 3). PBMC from healthy and HIV infected subjects secreted similar levels of IFNα and IFNγ in the absence of stimulation or in the presence of control ODN lacking the CpG motif (FIG. 3). Upon stimulation with CpG D ODN, however, PBMC from HIV infected subjects generated significantly lower IFNγ (p<0.05) or IFNα than healthy controls (p<0.001) (FIG. 3). The reduction in IFNα and IFNγ secretion correlated directly with the number of CD4+ T cells (p<0.01) (FIG. 5) and inversely with viral load (p<0.05), but did not correlate with the number of CD56+ NK cells or CD14+ monocytes. The reduced response to D ODN did not associate with antiretroviral therapy (ART).

TABLE 3

Description of HIV-infected PBMC Donors

|  |  | <200 | 200-500 | >500 |
|---|---|---|---|---|
| number |  | 9 | 17 | 17 |
| age |  | 40 +/− 2 | 39 +/− 1 | 37 +/− 2 |
| race | white | 4 | 13 | 8 |
|  | black | 4 | 4 | 7 |
|  | hispanic | 1 | 1 | 2 |
| gender | male | 8 | 15 | 17 |
|  | female | 0 | 2 | 0 |
| CD4 |  | 25 +/− 7 | 317 +/− 20 | 735 +/− 67 |
| % CD4T |  | 3 +/− 1 | 21 +/− 1.9 | 31 +/− 3 |
| Avg. VL |  | 27000 +/− 50000 | 1828 +/− 29000 | 663 +/− 330 |
| Range VL |  | 50-75 × 10⁸ | 50-5 × 10⁸ | ND-35000 |
| NK CD56+/CD16+ |  | 9 +/− 2 | 8.3 +/− 1 | 5.6 +/− 1.6 |
| % CD14 |  | 19 +/− 2 | 22 +/− 1 | 15.6 +/− 3 |
| % CD19 |  | 19 +/− 5 | 14 +/− 1 | 9 +/− 2 |
| % on HAART |  | 66 | 66 | 80 |

CPG D ODNs induce monocytes to mature into CD83+ CD86+ DC in vitro. Fewer mature DC were evident in PB from HIV infected patients, especially in those with higher viral loads. However, upon stimulation with CpG D ODN, a 10-fold increase in the number of mature DC was apparent.

The response to K ODN was not significantly different in PBMC from HIV infected and healthy subjects (FIG. 3) indicating that B cells and monocytes retain their ability to respond to CpG ODN. Together these data show that PBMC from HIV infected subjects are activated by CpG ODN in vitro. The responsiveness to CpG ODN, although reduced, is evident even among patients with high viral loads and low CD4+T cells.

Example 4

PBMC from SIV Infected Rhesus Macaques Respond to CpG ODN

Figure 6:
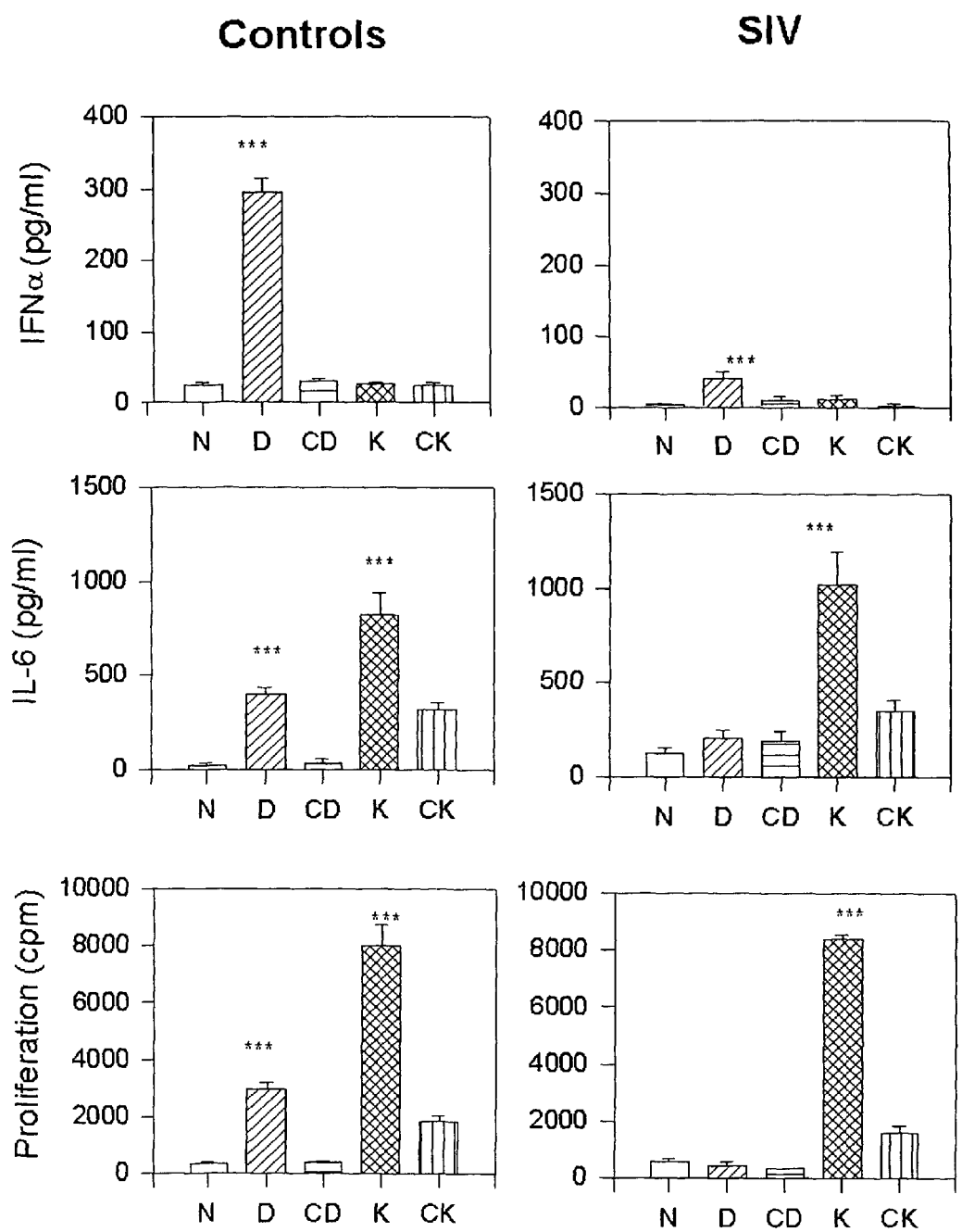
FIG. 6 is a set of graphs showing that, as observed with PBMC from HIV infected patients, PBMC from SIV infected macaques showed a response to CpG K ODN stimulation in vitro that was indistinct from that of healthy macaques. Stimulation with CpG D ODNs, in turn, generated significantly increased levels of IFNα, although the magnitude of the IFNα response was reduced when compared with PBMC from healthy macaques.

Rhesus macaques are a relevant animal model for testing the activity of CpG ODN planned for human use. It has been demonstrated that D and K ODN elicit a cytokine profile in PBMC of rhesus macaque that is similar to the one generated in human PBMC. To assess whether PBMC from rhesus macaques infected with SIV would respond to CpG ODN in vitro, PBMC from 16 SIV infected and 20 healthy macaques were stimulated in vitro with D and K CpG ODN. As observed with PBMC from HIV infected patients, PBMC from SIV infected macaques showed a response to CpG K ODN stimulation in vitro that was indistinct from that of healthy macaques (FIG. 6). Stimulation with CpG D ODN, in turn, generated significantly increased levels of IFNα, although the magnitude of the IFNα response was reduced when compared with PBMC from healthy macaques.

Example 5

Figure 7:
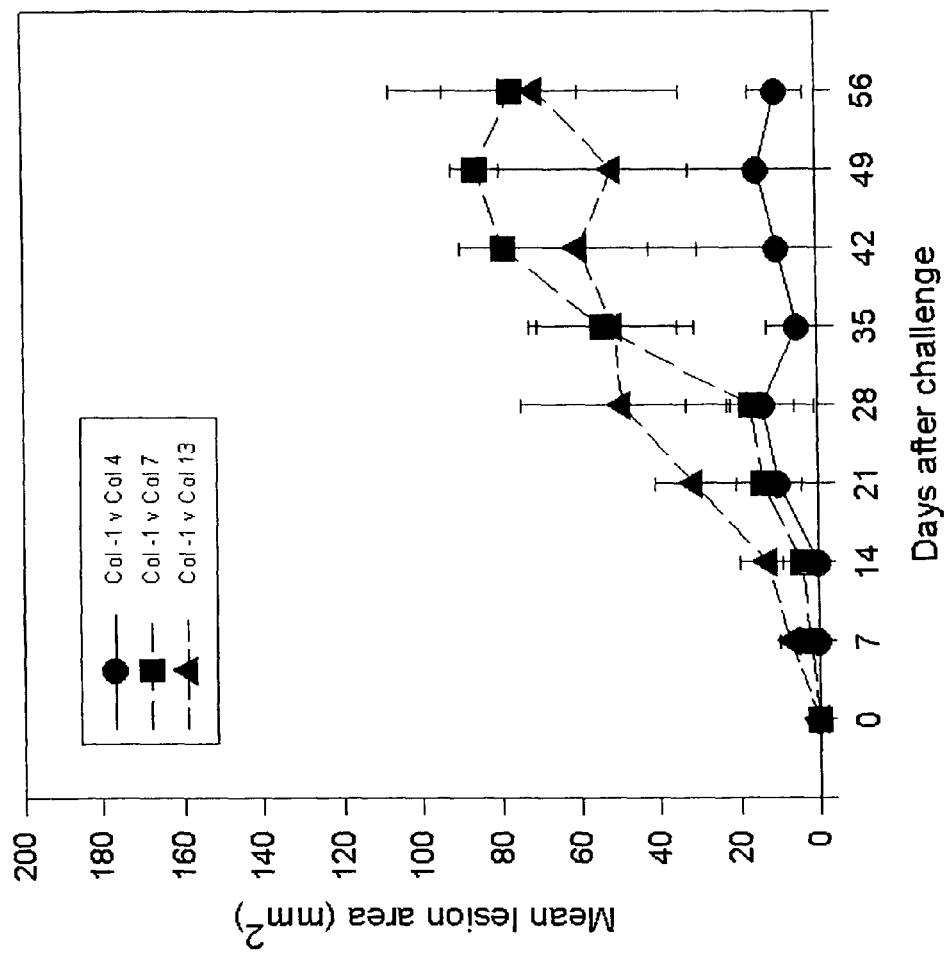
FIG. 7 is a graph showing lesion size in SIV-infected rhesus macaques challenged with *L. Major*. Fourteen rhesus macaques that had been infected with XX SIV strain mac239 a year before the start of the study (Viral load range: 0.3-28× $10^6$ copies/ml) were utilized. Monkeys were treated intradermally with D ODNs (n=4), K ODNs (n=4), control ODNs (n=3) or saline 3 days before and 3 days after an intradermal challenge with $10^7$ viable metacyclic promastigotes of *L. major* (WHOM/IR/-/173), a strain of *Leishmania* that frequently infects HIV patients. Control monkeys developed a typical self-limited in situ lesion characterized by erythema, induration, and ulceration. The lesion size, which reflects the severity of infection, was measured weekly. Monkeys treated with D ODNs had significantly smaller lesions than control or K ODN treated monkeys. The protection afforded to SIV infected macaques was comparable to that obtained in healthy monkeys.

CpG ODN Protect SIV Infected non-human Primates From a Cutaneous Infection with L. Major To assess whether the response to CpG ODN generated in immunosuppressed HIV patients would suffice to generate an immunoprotective response in vivo, 14 rhesus macaques that had been infected with XX SIV strain mac239 a year before the start of the study (Viral load range: $0.3\text{-}28 \times 10^6$ copies/ml) were utilized. Monkeys were treated i.d. with D ODN (n=4), K ODN (n=4), control ODN (n=3) or saline 3 days before and 3 days after an intra-dermal challenge with $10^7$ viable metacyclic promastigotes of L. major (WHOM/IR/-/173), a strain of Leishmania that frequently infects HIV patients. As shown in FIG. 7, control monkeys developed a typical self-limited in situ lesion characterized by erythema, induration, and ulceration. The lesion size, which reflects the severity of infection (Amaral, et al., 1996, Exp. Parasitol. 82:34), was measured weekly. Monkeys treated with CpG D ODN had significantly smaller lesions than control or K ODN treated monkeys. On day 56 the monkeys were euthanized and the local and systemic parasite burden measured. Monkeys treated with D ODN appeared to have a 1 log reduction in parasite burden at the lesion site compared to the ones treated with control ODN or saline but the difference did not reach statistical significance. No systemic diffusion of the parasites were evident on any of the groups.

Lastly, since vaccination and infection can activate the immune cells and lead to an increase in viremia, the viral load of the macaques was assessed every 2 weeks throughout the study. No significant change in viral load was evident in any of the groups.

Example 6

CpG ODN Protect p47phox-/-mice From Infection with Listeria p47phox-/-mice exhibit a phenotype similar to that of human chronic granulomatous disease (CGD). The biochemical basis for CGD is a defect in the phagocyte nicotine amide dinucleotide phosphatase (NADPH) oxidase, the enzyme responsible for producing superoxide O-2, which in turn is critical for host defense against bacterial and fungal infection. Mice were treated with CpG or saline 3 days before and 3 days after a challenge with Listeria bacteria Mice pretreated with CpG D ODNs showed a 20% increase in protection against Listeria as compared to those treated with control ODN or saline.

Example 7

PBMC from Subjects with Human Chronic Granulomatous Disease (CGD) Respond to CpG ODN The biochemical basis for CGD is a defect in the phagocyte nicotine amide dinucleotide phosphatase (NADPH) oxidase, the enzyme responsible for producing superoxide O-2, which in turn is critical for host defense against bacterial and fungal infection. In order to assess whether PBMC from subjects with CGD are responsive to CpG ODN activation, the response of PBMC from subjects with CGD and healthy individuals to D and K CpG ODNs is compared in vitro. The response elicited by PBMC from healthy subjects to the two types of CpG ODN is distinct: D ODN trigger the secretion of IFNα and IFNγ, and induce DC maturation. In contrast, K ODN increase cell proliferation and IL-6 production. IFNα and IFNγ levels in PBMC from healthy and subjects with CGD are measured as described above following stimulation with D and K CpG ODN.

Example 8

CpG Oligonucleotides Improve the Response to Hepatitis B Immunization in Healthy and SIV Infected Rhesus Macaques Development of an immunogenic vaccine against hepatitis B is particularly important for HIV infected patients. Since shared epidemiological risks result in HIV infected subjects having a high incidence of HBV, and co-infection with HBV increases the rate of hepatotoxicity of HAART. Although HBV vaccination is recommended to all HIV patients, its efficacy in these patients is reduced. This example compares the adjuvant effect of K and D type ODN as vaccine adjuvants to the hepatitis B vaccine and compares their effectiveness immunocompromised SIV infected rhesus macaques.

ODNs were synthesized as follows:

| D19: | GGtgcatcgatgcagGGGGG | (SEQ ID NO: 176) |
| D35: | GgtgcatcgatgcaggggGG | (SEQ ID NO: 177) |
| D29: | GGtgcaccggtgcagGGGGG | (SEQ ID NO: 178) |
| K3: | ATCGACTCTCGAGCGTTCTC | (SEQ ID NO: 179) |
| K123: | TCGTTTGTTCT | (SEQ ID NO: 180) |
| K23: | TCGAGCGTTCTC | (SEQ ID NO: 181) |

Phosphorothioate bases are shown in capital letters; phosphodiester bases in lower case. All ODN had less than <0.1 EU of endotoxin per mg of ODN as assessed by a Limulus amebocyte lysate assay (QCL-1000, BioWhittaker). Due to individual heterogeneity in the response to specific "K" and "D" sequences mixtures of ODN were used in in vivo studies.

Two to three year old rhesus macaques (M. mulata) were obtained from the FDA colony in South Carolina. Animals were monitored daily by veterinarians. No systemic or local adverse reactions to CpG ODN were observed.

SIV plasma RNA levels were determined by a real time RT-PCR assay, as described in Example 1. IgG antibodies to HBs were assessed as per manufacturer's instructions and quantitated using IgG anti-Hepatitis B surface antigen (anti-HBs, DiaSorin, Saluggia, Italy). Spearman's correlations were used to assess the relationship between viral load and response to ODN. Differences in antibody titers over time were tested by Friedman Repeated-Measures Analysis on Ranks with Tukey's All Pairwise Multiple Comparison Procedure using Sigma Stat (SPSS, San Rafael, Calif.). Differences in viral load were tested by t test of log-normalized data.

Figure 8:
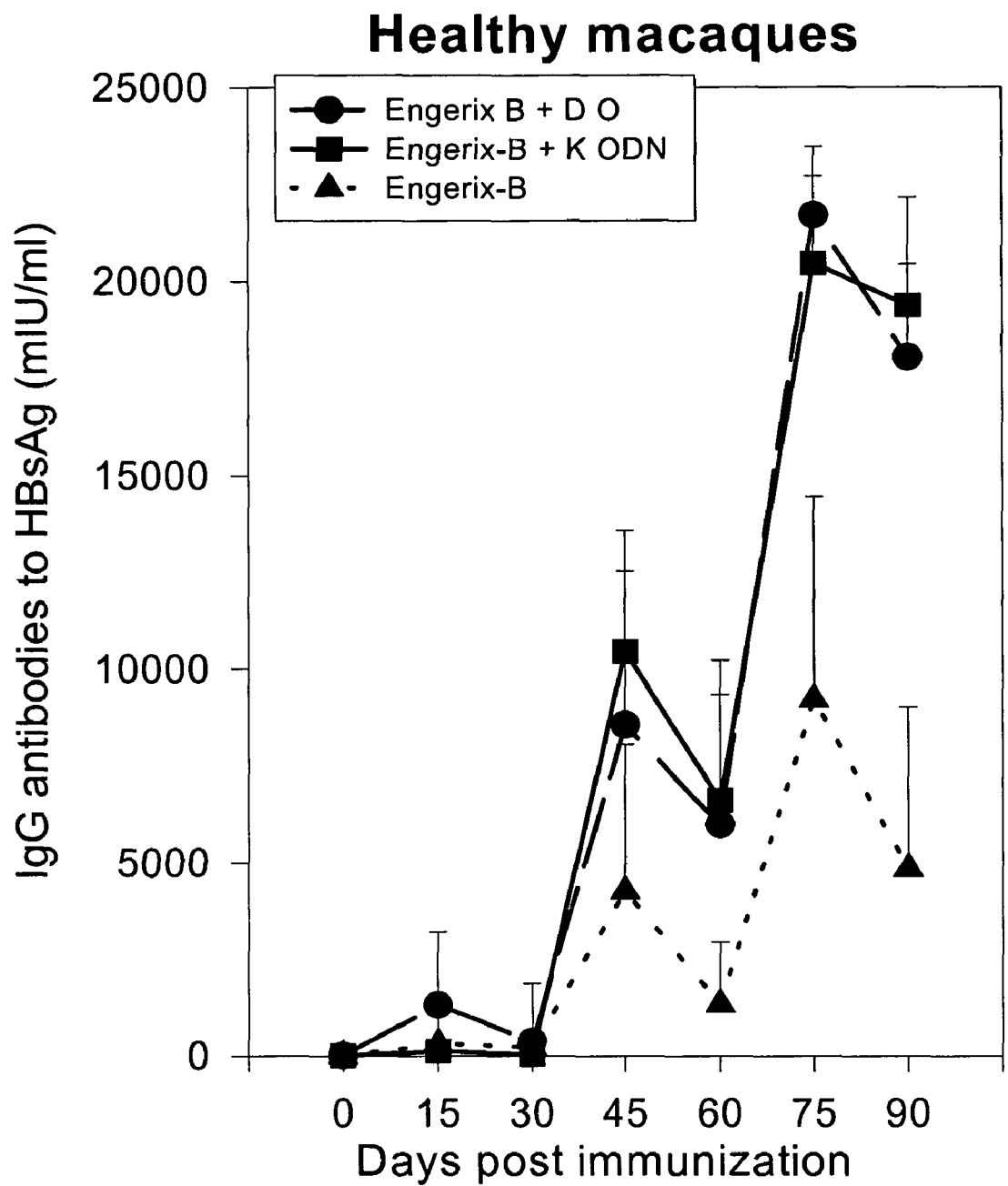
FIG. 8 is a graph showing the effect of D and K ODN as adjuvants to the hepatitis B vaccine in rhesus macaques. Macaques (five/group) were immunized with hepatitis B vaccine ENGERIX-B™ (10 μg) alone or together with D or K ODN (250 μg/dose) on days 1, 30 and 60 of the study. Levels of IgG anti-hepatitis B surface antigen (HbsAg) were monitored by ELISA every two weeks. Macaques that received D or K ODN together with the vaccine developed significantly higher antibody levels compared to those that received the vaccine alone ($p<0.01$).

To compare the efficacy of D and K type ODN as adjuvants for the vaccine against hepatitis B, 15 two year-old rhesus macaques weighing 6+/−1 lbs. (five per group) were immunized with the pediatric dose of ENGERIX-B™ containing 10 μg of HBsAg adsorbed to alum alone or together with 250 μg of D or K type ODN. The animals were boosted 30 and 60 days later with the same product. All monkeys were negative for antibodies to HbsAg at baseline. Fourteen days after the first immunization, all macaques vaccinated with ENGERIX-B™-D ODN had antibodies to HBV greater than 10 mIU/ml, compared to only 60 and 80% of those immunized with ENGERIX-B™ K ODN or ENGERIX-B™ alone respectively. All animals developed protective levels (>10 mIU/ml) of antibodies to HBV after the first boost. As shown in FIG. 8, animals that received K or D ODN as adjuvants developed significantly higher antibody levels (peak titer: 20469+/−2240 and 21702+/−1764 for K and D ODN respectively, compared to 9226+/−5237 for those animals that received the vaccine alone, p=0.012). D and K type CpG ODN were equally effective as vaccine adjuvants for the hepatitis B vaccine.

Figure 9:
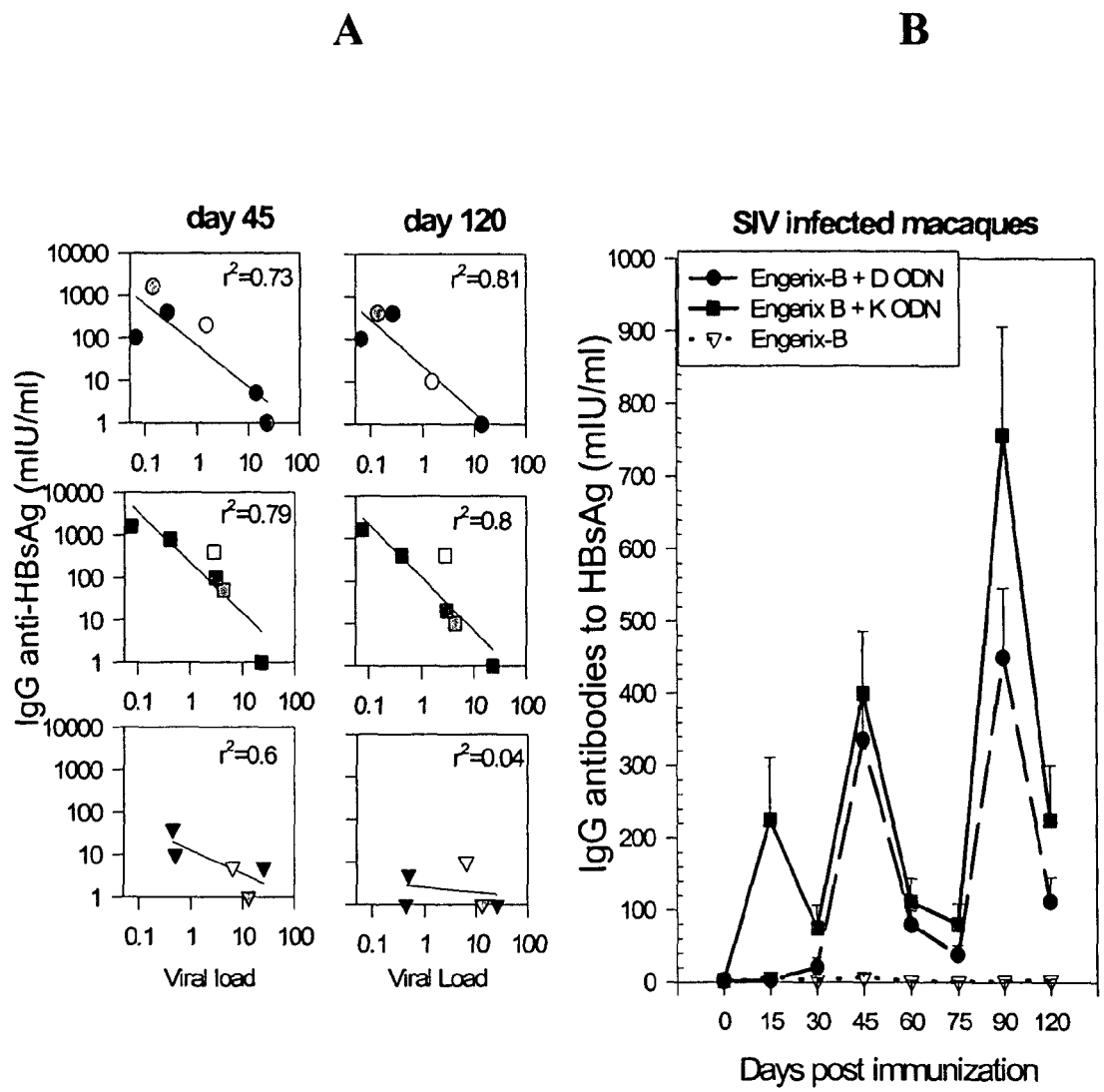
FIGS. 9A-B is a pair of graphs showing that D and K ODN boost the immunogenicity of hepatitis B vaccine ENGERIX-B™ in SW-infected rhesus macaques. SW infected macaques were immunized on days 1, 30 and 75 with hepatitis B vaccine ENGERIX-B™ alone (n=5) or together with D or K ODN (n=6/group). Levels of IgG anti-HbsAg were monitored as described in Example 8.

Next, the efficacy of CpG ODN in eliciting a similar increase in antibodies to HbsAg in SIV infected rhesus macaques was assessed. Seventeen SIV infected animals were immunized with a pediatric dose of hepatitis B vaccine ENGERIX-B™ alone or together with 250 μg of D or K ODN. The animals were boosted 30 and 75 days after prime. The levels of IgG anti-HbsAg in sera were measured every two weeks for four months. Unlike healthy macaques, SIV infected animals were unable to mount a protective antibody response when immunized with the commercial hepatitis B vaccine alone, even after three immunizations. Only 20% of the animals immunized with ENGERIX-B™ alone had antibody levels greater than 10 mIU/ml, and the mean peak level of antibodies produced was 9+/−7 mIU/ml. Among the animals that received the vaccine together with D or K ODN, the antibody titers achieved were inversely correlated with monkey's viral load at the start of the study (FIG. 9A). Indeed, animals with viral loads greater than $1 \times 10^7$ copies/ml at the time of immunization were unable to mount a protective response to the vaccine regardless of the adjuvant used. Among those that had viral loads greater than $10^7$ copies/ml, K and D ODN were similarly effective at promoting the development of anti-HbsAg antibodies (FIG. 9B). Although the antibody levels achieved were significantly increased relative to those macaques receiving the HBV vaccine alone, their absolute levels were significantly lower than those developed by healthy macaques (p<0.001).

No significant increases in viral load were observed for any of the groups during this experiment, indicating that at this dose, CpG ODN do not appear to impact viral replication.

As demonstrated in this example, addition of K or D ODN boosts the immunogenicity of the HBV vaccine to render refractory SIV infected macaques responsive to vaccination. There is a pressing need for the development of an immunogenic vaccine against hepatitis B that is effective in HIV infected patients. These findings indicate that addition of CpG ODN to commercially available vaccines may allow patients with low or moderate viral loads to mount a protective response.

It will be apparent that the precise details of the methods or compositions described may be varied or modified without departing from the spirit of the described disclosure. We claim all such modifications and variations that fall within the scope and spirit of the claims below.

The invention claimed is:

1. A method of increasing an immune response to an opportunistic infection in an immunocompromised subject comprising
    selecting an immunocompromised subject infected with a secondary infection, wherein the immunocompromised subject is immunocompromised as a result of an infection with human immunodeficiency virus (HIV) or a simian immunodeficiency virus (SIV), and wherein the secondary infection is infection with a *Leishmania*;
    administering to the immunocompromised subject infected with the secondary infection a therapeutically effective amount of an oligodeoxynucleotide comprising the nucleic acid sequence set forth as SEQ ID NO: 176, an oligodeoxynucleotide comprising the nucleic acid sequence set forth as SEQ ID NO: 177 and an oligodeoxynucleotide comprising the nucleic acid sequence set forth as SEQ ID NO: 178; and
    assessing the immune response to the *Leishmania* in the subject;
    thereby increasing the response to the *Leishmania* in the immunocompromised subject.

2. The method of claim 1, wherein the human immunodeficiency virus is HIV-1.

3. The method of claim 1, wherein the human immunodeficiency virus is HIV-2.

4. The method of claim 1, wherein the subject has acquired immune deficiency syndrome (AIDS).

5. The method of claim 1, wherein one or more of nucleotides 3-15 of SEQ ID NO: 176, nucleotides 2-18 of SEQ ID NO: 177, or nucleotides 3-15 of SEQ ID NO: 178 comprise phosphodiester bases.

6. The method of claim 1, wherein nucleotides 3-15 of SEQ ID NO: 176, nucleotides 2-18 of SEQ ID NO: 177, and nucleotides 3-15 of SEQ ID NO: 178 are phosphodiester bases.

7. The method of claim 1, wherein one or more of nucleotides 1 or 2 of SEQ ID NO: 176, nucleotide 1 of SEQ ID NO: 177, or nucleotides 1 or 2 of SEQ ID NO: 178 comprise phosphorothioate bases.

8. The method of claim 1, wherein one or more of nucleotides 16-20 of SEQ ID NO: 176, nucleotides 19 or 20 of SEQ ID NO: 177, or nucleotides 16-20 of SEQ ID NO: 178 comprises phosphorothioate bases.

9. The method of claim 2, further comprising administering to the subject a combination of drugs which comprises a highly active anti-retroviral therapy (HAART).

10. The method of claim 1, further comprising administering an anti-retroviral drug.

11. The method of claim 10, wherein the anti-retroviral drug comprises 3'-azido-3' dexoy-thymidine (AZT).

12. A method of increasing an immune response to an opportunistic infection with a pathogen in an immunocompromised subject, comprising
    selecting an immunocompromised subject wherein the subject is immunocompromised as a result of an infection with a human immunodeficiency virus; and
    administering to the subject a therapeutically effective amount of an oligodeoxynucleotide comprising the nucleic acid sequence set forth as SEQ ID NO: 176, an oligodeoxynucleotide comprising the nucleic acid sequence set forth as SEQ ID NO: 177 and an oligodeoxynucleotide comprising the nucleic acid sequence set forth as SEQ ID NO: 178,
    wherein an antigenic epitope of a polypeptide from the pathogen is not administered to the subject,
    thereby increasing the response to the opportunistic infection, wherein the pathogen is a *Leishmania*.

* * * * *